(12) United States Patent
Martinson

(10) Patent No.: US 9,301,722 B1
(45) Date of Patent: Apr. 5, 2016

(54) GUIDING COMPUTATIONAL PERCEPTION THROUGH A SHARED AUDITORY SPACE

(71) Applicant: TOYOTA JIDOSHA KABUSHIKI KAISHA, Toyota-shi, Aichi-ken (JP)

(72) Inventor: Eric Martinson, Mountain View, CA (US)

(*) Notice: Subject to any disclaimer, the term of this patent is extended or adjusted under 35 U.S.C. 154(b) by 171 days.

(21) Appl. No.: 14/171,662

(22) Filed: Feb. 3, 2014

(51) Int. Cl.
*G10L 21/06* (2013.01)
*G10L 25/06* (2013.01)
*A61B 5/00* (2006.01)

(52) U.S. Cl.
CPC .................................. *A61B 5/7405* (2013.01)

(58) Field of Classification Search
None
See application file for complete search history.

(56) References Cited

U.S. PATENT DOCUMENTS

| | | | | |
|---|---|---|---|---|
| 6,853,880 B2* | 2/2005 | Sakagami | ............ | G06N 3/008 318/568.2 |
| 7,076,430 B1* | 7/2006 | Cosatto | ............ | G10L 21/06 704/272 |
| 7,844,467 B1* | 11/2010 | Cosatto | ............ | G06T 13/40 704/231 |
| 8,131,551 B1* | 3/2012 | Cosatto | ............ | G10L 15/1807 704/246 |
| 2006/0149824 A1* | 7/2006 | Park | ............ | H04L 69/26 709/206 |
| 2008/0071540 A1* | 3/2008 | Nakano | ............ | G10L 15/20 704/251 |

FOREIGN PATENT DOCUMENTS

JP 2002-501208 1/2002

OTHER PUBLICATIONS

Aarabi, "The fusion of distributed microphone arrays for sound localization", EURASIP Journal on Applied Signal Processing, 2003, 338-347 (10 pages).
Droeschel, et al., "Learning to interpret pointing gestures with a time-of-flight camera." Proceedings of 6th International Conf. on Human-Robot Interaction (HRI). Lausanne, Switzerland: ACM (2011) (8 pages).
Martinson, et al., "Discovery of Sound Sources by an Autonomous Mobile Robot." Autonomous Robots, 27 (2009) (26 pages).
Martinson, et al., "Fighting fires with human-robot teams." Proceedings of Int. Conf. on Intelligent Robots and Systems. Villamoura, Portugal: IEEE (2012) (2 pages).
Volgyesi, et al., "Shooter localization and weapon classification with soldier-wearable networked sensors." Proceedings of MobiSys, (pp. 113-126). San Juan, Puerto Rico (2007) (14 pages).

* cited by examiner

*Primary Examiner* — Marcus T Riley
(74) *Attorney, Agent, or Firm* — Patent Law Works LLP

(57) ABSTRACT

In an example, a computer-implemented method receives one or more user inputs and captures a sound associated with a sound source via one or more capturing devices using sound source localization. The method then estimates one or more first posterior likelihoods of one or more positions of the sound source based on the one or more user inputs and a second posterior likelihood of a position of the sound source based on the sound. The method then estimates an overall posterior likelihood of an actual position of the sound source based on 1) the one or more first posterior likelihoods of the one or more positions of the sound source estimated based on the one or more user inputs and 2) the second posterior likelihood of the position of the sound source estimated based on the sound.

27 Claims, 22 Drawing Sheets

GUIDING COMPUTATIONAL PERCEPTION THROUGH A SHARED AUDITORY SPACE

BACKGROUND

The specification relates to guiding computational perception through a shared auditory space.

Blindness is an age-related disease. As the world's population continues to get older, the number of blind and visually impaired individuals will likely only increase. These individuals often want to know about what they hear in the world around them. They want to know what other people can "see". Existing systems fail to provide an effective solution that can help these individuals learn about arbitrary objects that they can only hear about, that they do not know the exact location of, or that they do not know uniquely identifiable traits about.

In some cases, guide dogs, which are probably the most well-known aide outside the blind community, are used to help these individuals. However, these dogs are expensive to train, require a lot of work to keep, and are capable of serving these individuals only for a limited number of years. While these guide dogs provide available services, as the blind population grows, providing guide dogs to all these individuals is not realistic.

Today, a robot is capable of watching a lot of objects and/or actions in its surroundings including people, cars, advertisements, etc. Sizable online databases even allow real-time training for computational perception, to create new classifiers on the fly as needed. However, such a robot generally cannot run an endless number of classifiers all the time. It is too computationally intensive, would likely generate too many false positives with even the best of classifiers, and would overwhelm a human user associated with its corresponding system. Some existing robotic solutions have demonstrated how a human can guide the system using gesture or speech and some include robots that are configured to localize sound sources using onboard microphone arrays. However, these solutions generally only utilize what a single agent can detect about an object of interest. For instance, these solutions take into consideration either what a human has detected or what a robot has detected about the object of interest but generally not both. As a result, these solutions often lead to poor accuracy, ambiguity, and can lead to poor guidance for other computational perception systems.

Some existing solutions can find objects of interest in a visual space and then guide a computer vision system to the right target. For audible objects, sound source localization has been used to guide other sensors, but not generally in conjunction with what a human can hear. For instance, in some popular solutions, GPS location is used to query a mobile computer about its surroundings. However, these solutions have difficulty identifying transient sources of noises. In particular, these solutions often fail to query about sources that move or are short in duration because they do not persist long enough to be queried by GPS proximity. Other existing solutions use pointing gestures in Human-Robot interaction to guide a robot to a target in multiple perceptual domains. However, these solutions often generally require a shared visual space between a human and a computer exist and are therefore inflexible. In another solution, multi-array sound source localization is used to identify audible objects. Although this solution can identify auditory objects of interest, it suffers from significant limitations. For instance, this solution assumes that all sensors are microphone arrays having similar capabilities and limitations, which is impractical. In addition, a user using this solution would have to wear additional hardware in order to triangulate accurately on the source location. Further, the solution accounts for only one type of stimuli, which is often not unique enough to be of interest to a user. As a result, any other sounds that the user might be interested in would have to be pre-specified and trained, which is time consuming and computationally expensive.

SUMMARY

In various embodiments, this specification describes a technology for querying a computing device, such as a robot, about unknown audible objects in a surrounding environment through a combination of computational sound source localization and human inputs including, for instance, pointing gestures and spoken descriptors. According to one innovative aspect of the subject matter described in this specification, a system includes one or more processors and one or more memories storing instructions that, when executed by the one or more processors, cause the system to receive one or more user inputs; capture a sound associated with a sound source via one or more capturing devices using sound source localization; estimate one or more first posterior likelihoods of one or more positions of the sound source based on the one or more user inputs; estimate a second posterior likelihood of a position of the sound source based on the sound; and estimate an overall posterior likelihood of an actual position of the sound source based on 1) the one or more first posterior likelihoods of the one or more positions of the sound source estimated based on the one or more user inputs and 2) the second posterior likelihood of the position of the sound source estimated based on the sound.

In general, another innovative aspect of the subject matter described in this disclosure may be embodied in methods that include receiving, using one or more computing devices, one or more user inputs; capturing, using the one or more computing devices, a sound associated with a sound source via one or more capturing devices using sound source localization; estimating, using the one or more computing devices, one or more first posterior likelihoods of one or more positions of the sound source based on the one or more user inputs; estimating, using the one or more computing devices, a second posterior likelihood of a position of the sound source based on the sound; and estimating, using the one or more computing devices, an overall posterior likelihood of an actual position of the sound source based on 1) the one or more first posterior likelihoods of the one or more positions of the sound source estimated based on the one or more user inputs and 2) the second posterior likelihood of the position of the sound source estimated based on the sound.

Other aspects include corresponding methods, systems, apparatus, and computer program products for these and other innovative aspects.

These and other implementations may each optionally include one or more of the following features and/or operations. For instance, the operations include: fusing, using the one or more computing devices, the one or more first posterior likelihoods of the one or more positions of the sound source and the second posterior likelihood of the position of the sound source to produce the overall posterior likelihood; that the one or more first posterior likelihoods include two or more posterior likelihoods estimated based on two or more user inputs; that fusing the two or more first posterior likelihoods and the second posterior likelihood includes combining, using the one or more computing devices, the two or more first posterior likelihoods into a combined posterior likelihood, scaling, using the one or more computing devices, the combined posterior likelihood, and combining the scaled combined posterior likelihood with the second posterior likelihood; that the one or more user inputs include a user gesture and a user body pose; that receiving the one or more user inputs further includes determining a gesturing direction from the user gesture and determining one or more of a position and orientation from the user body pose; that estimating the one or more first posterior likelihoods further includes estimating a gesture-pose-based posterior likelihood of a position of the sound source based on the gesturing direction and the one or more of the position and orientation associated with the user body pose; that the one or more inputs include a user speech segment and a user body pose; that receiving the one or more user inputs further includes determining a direction from the user speech segment and determining one or more of a position and orientation from the user body pose; that estimating the one or more first posterior likelihoods further includes estimating a speech-pose-based posterior likelihood of a position of the sound source based on the direction associated with the speech segment and the one or more of the position and orientation associated with the user body pose; that estimating the one or more first posterior likelihoods further includes generating one or more first evidence grids of likely sound source positions based on the one or more user inputs, the one or more first evidence grids reflecting the one or more first posterior likelihoods, respectively; that estimating the second posterior likelihood further includes generating a second evidence grid of likely sound source positions based on the sound, the second evidence grid reflecting the second posterior likelihood; that estimating the overall posterior likelihood of the actual position of the sound source further includes combining the one or more first evidence grids and the second evidence grid; and guiding, using the one or more computing devices, a mobile computing device to the actual position of the sound source. For instance, the features include that the one or more user inputs include one or more of a user gesture, a user speech segment, and a user body pose; and the one or more capturing devices includes one or more of an image capturing device, a video capturing device, and an audio capturing device.

The technology described herein is particularly advantageous in a number of respects. For example, the technology can improve the ability of a user, such as a blind or visually impaired individual, to ask directed queries about the environment around them; can limit the search space and generate better targeted information; use sound as a shared medium, which is a natural interface for the blind individual, as compared to other approaches requiring a shared visual space; and can incorporate human gestures and speech in auditory localization, which eliminates the need for on-body hardware. It should be understood that the foregoing advantages are provided by way of example and the technology may have numerous other advantages and benefits.

The disclosure is illustrated by way of example, and not by way of limitation in the figures of the accompanying drawings in which like reference numerals are used to refer to similar elements.

DETAILED DESCRIPTION

According to some embodiments, the technology described in this specification makes use of a shared auditory space, using both what a computer can hear and what a person can hear, to locate a sound source and guide a mobile computing device such as a robot equipped with visual sensors, to the sound source. More specifically, in one example, the technology can detect and convert verbal (e.g. speech) and/or non-verbal (e.g. gestural) cues localizing a sound source of interest into probabilistic representations of sound source likelihoods, referred to herein in some embodiments as first posterior likelihoods. The technology can then fuse the first posterior likelihoods with a second posterior likelihood computed by the technology using computational sound source localization (SSL) estimated on real-time microphone array data. The technology can then find a position that maximizes the fused likelihood to distinguish the sound source of interest from other sounds in an environment. That position can then be used to guide a mobile computing device such as a robot to the sound source of interest or for other purposes.

System Overview

Figure 1:
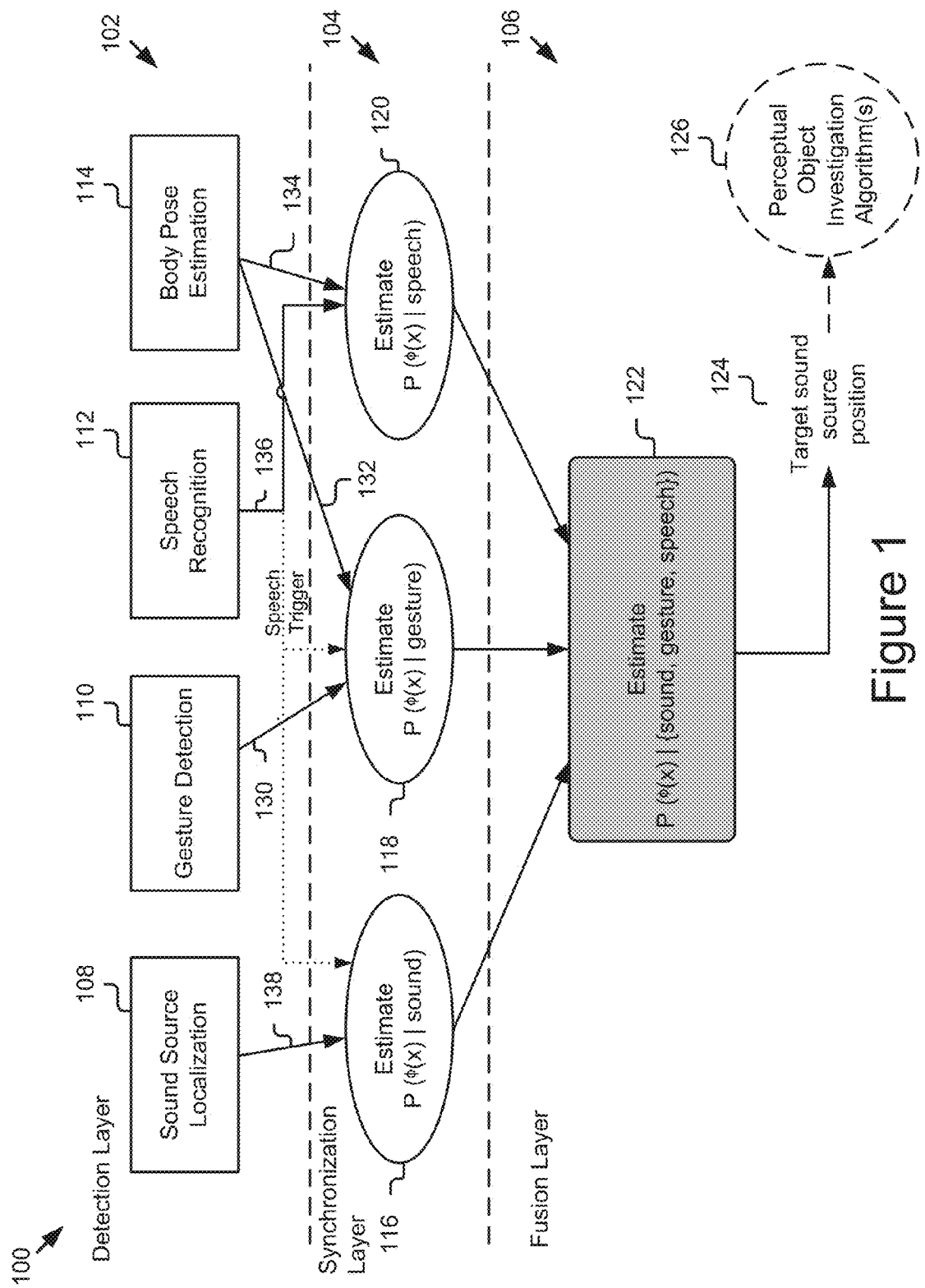
FIG. 1 is a block diagram illustrating an example shared auditory perception architecture.

FIG. 1 illustrates a block diagram of an example shared auditory perception architecture 100. The illustrated architecture 100 has three layers including a detection layer 102, a synchronization layer 104, and a fusion layer 106. The detection layer 102 includes four distinct perceptual components: sound source localization 108, gesture detection 110, speech recognition 112, and body pose estimation 114, each of which are described in more detail below.

Sound Source Localization 108

Utilizing one or more capturing devices, such as a microphone array, a sound source localization module 822 (e.g., see FIG. 8B) may identify probable sound source locations, such as directions, Cartesian positions, etc. In some embodiments, the one or more capturing devices may localize sound sources by determining differences between signals arriving at capturing devices (e.g., different microphones in the array) and comparing them to the physics of in-air sound propagation.

In some embodiments, the sound source localization module 822 may use an implementation of the machine listening toolbox (HARK) and the MUSIC (MUltiple SIgnal Classification) algorithm for SSL, although other approaches may also be used. In some embodiments, the sound source localization module 822 may combine the MUSIC algorithm with a tracking algorithm to filter localization angles and assign an ID to a sound source. The sound source localization module 822 may require, in some instances, a pre-specified number of sound sources be determined prior to identifying the sound source locations. In some embodiments, to allow for the possibility that a sound source of interest is not the loudest and/or worst sound in an environment, the number of sound sources being detected and tracked may be set to a certain number, such as two.

Gesture Detection 110

The gesture detection module 824 (e.g., see FIG. 8B) may receive sensor data and process it to determine a user gesture. A user gesture includes a motion made by a body part of the user indicating a direction or action. Gestures may be captured by one or more sensors, such as depth-based skeletal tracking systems, range-based arm detection systems, and/or visual detection in RGB-D images.

Figure 9:
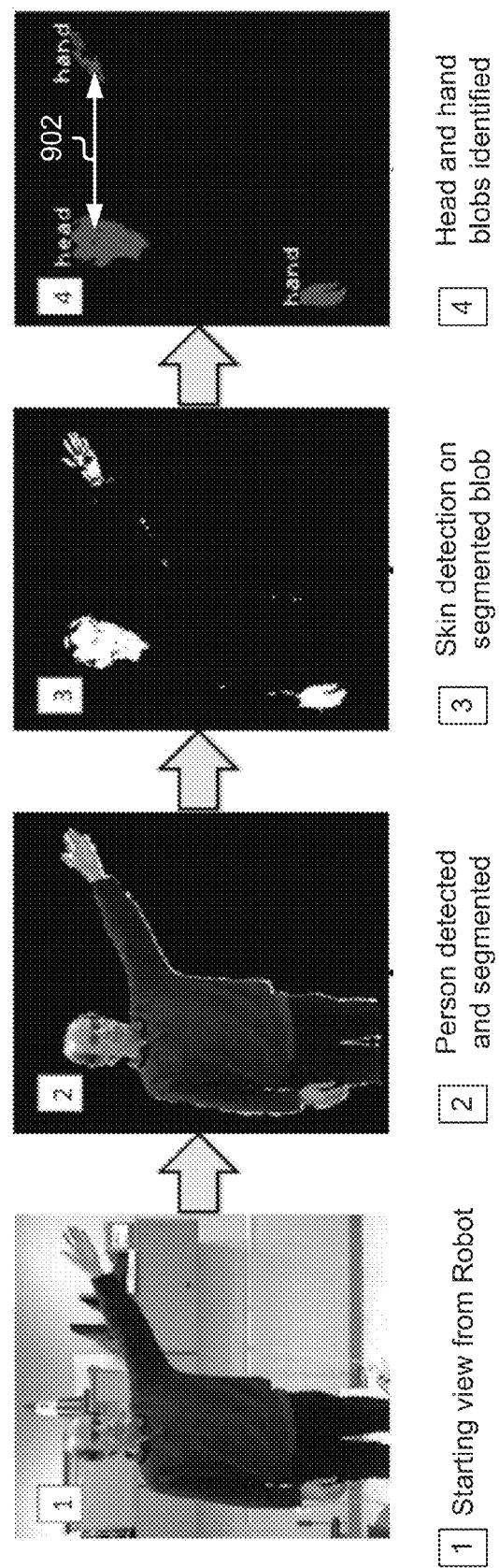
FIG. 9 is an example process for detecting a user pointing direction.

In some embodiments, the gesture detection module 824 performs hand detection and gesture recognition. For instance, the gesture detection module 824 may use a multi-level approach involving 3D and 2D data for hand detection and gesture recognition. The gesture detection module 824 may capture 3D depth information along with 2D color texture maps via the one or more sensors. The 3D depth information may first be processed to reliably segment human body (e.g., upper) blobs. For instance, as depicted in FIG. 9, the gesture detection module 824 may process a depth image recorded from the one or more sensors to identify blob(s) and may analyze the blob(s) to validate them as depicting human body. Next, the gesture detection module 824 may perform color segmentation on the 2D color texture maps or image regions corresponding to each blob segmented in the 3D depth information to detect human skin tones. In some embodiments, the gesture detection module 824 may perform skin tone segmentation using HSV color space having the following thresholds:

$$0° < H < 25° \text{ or } 335° < H < 360°,$$

$$0.2 < S < 0.6,$$

$$V \geq 40.$$

The result produced by the skin tone detection performed by the gesture detection module 824 on each of the segmented human body blobs may include a subset of blobs corresponding to the face and one or more hands of the person associated with the body blob. In some instances, one or both of the hands might be occluded due to position of the person in the scene or simply because the person's hands were not captured to begin with. The gesture detection module 824 may track the blobs corresponding to the face and hands independently, and use face detection, in parallel, to identify which blob belongs to the face. In some embodiments, upon identifying one of skin colored blobs as belonging to the face, the gesture detection module 824 may identify remaining blobs as hands.

In some embodiments, the gesture detection module 824 may identify a direction in which a user is pointing by determining a line from a point (e.g., from the center) of a face blob to a point (e.g., to the center) of a hand blob. For example, as shown in FIG. 9, the gesture detection module 824 may use the line 902 to determine that the person is pointing in the left direction.

Speech Recognition 112

Figure 10:
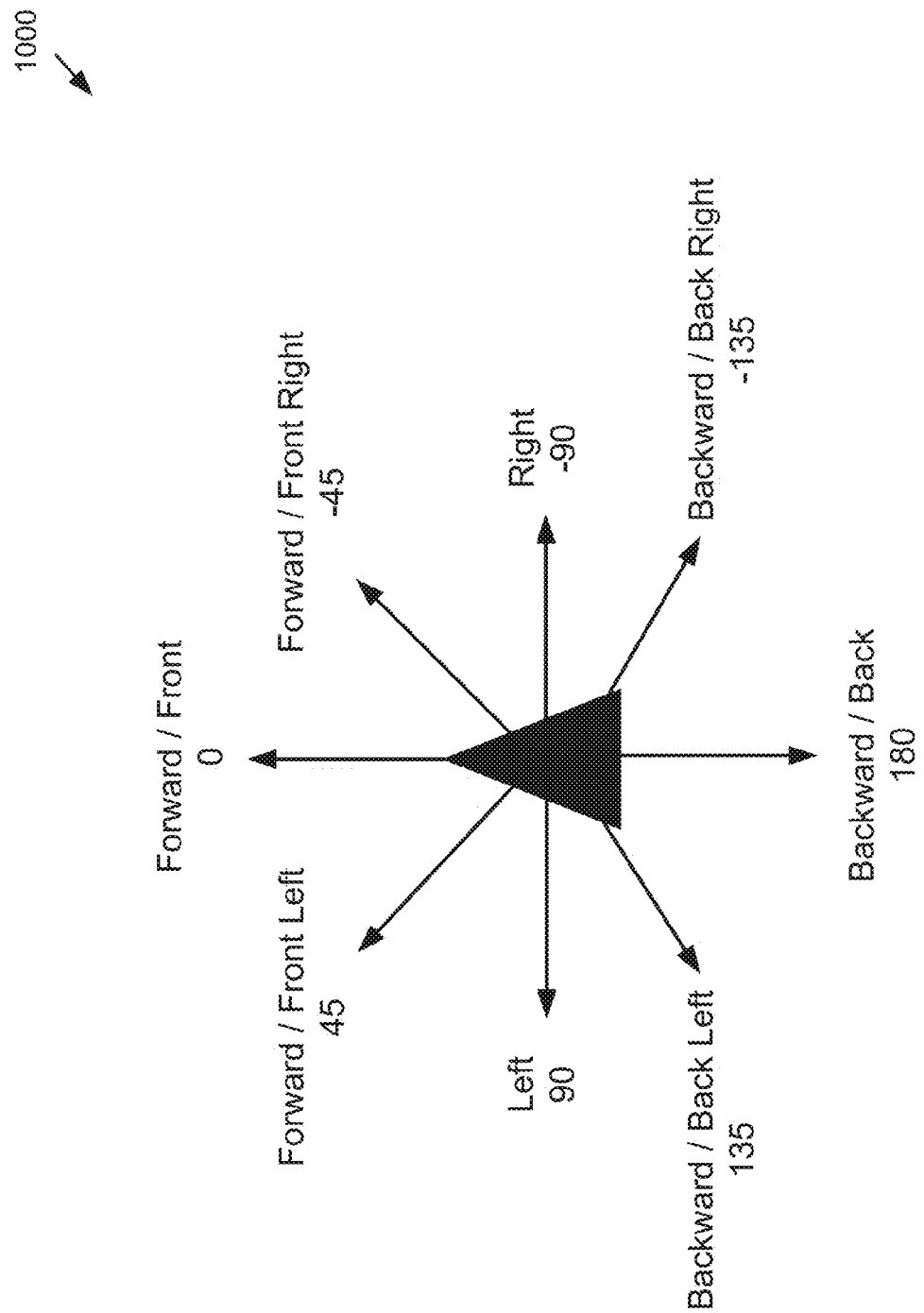
FIG. 10 depicts directions and angles associated with a set of user speech commands.

A user may use speech as a natural way of conveying a direction to a computing device (e.g., a robot, computer, etc.). In some embodiments, the user speech may be used to estimate a location of the sound source of interest. For instance, a user may indicate the location of the sound source to the computing device using a speech segment. The speech recognition module 826 (e.g., see FIG. 8B) may be capable of recognizing one or more user speech segments. A user speech segment may include a word, phrase, or command spoken by the user. In some instances, the speech segment may be directed by the user at a computing device, such as a robot. The one or more user speech segments may include one or more key orientation descriptors such as "left", "right", "forward", "backward", "up", and "down" that indicate direction to the source of interest in a human coordinate frame. FIG. 10 depicts an example direction and angle associated with each of the one or more key orientation descriptors. In some further examples, the speech segment may be provided in conjunction with a user gesture. For instance, the user might say, "it's over there" while simultaneously pointing in a particular direction.

Body Pose Estimation 114

The body pose estimation module 828 (e.g., see FIG. 8B) may detect a person following a robot and identify that person's body pose (e.g., position and/or orientation). In some embodiments, the body pose may be estimated relative to the one or more sensors (e.g., a microphone array). In some embodiments, a body pose including the user's body position and/or orientation may be combined by the body pose estimation module 828 with the user's gestured direction and/or the user's speech segment to determine a combined posterior likelihood of the sound source of interest as described below with reference to the synchronization layer 104.

Figure 11:
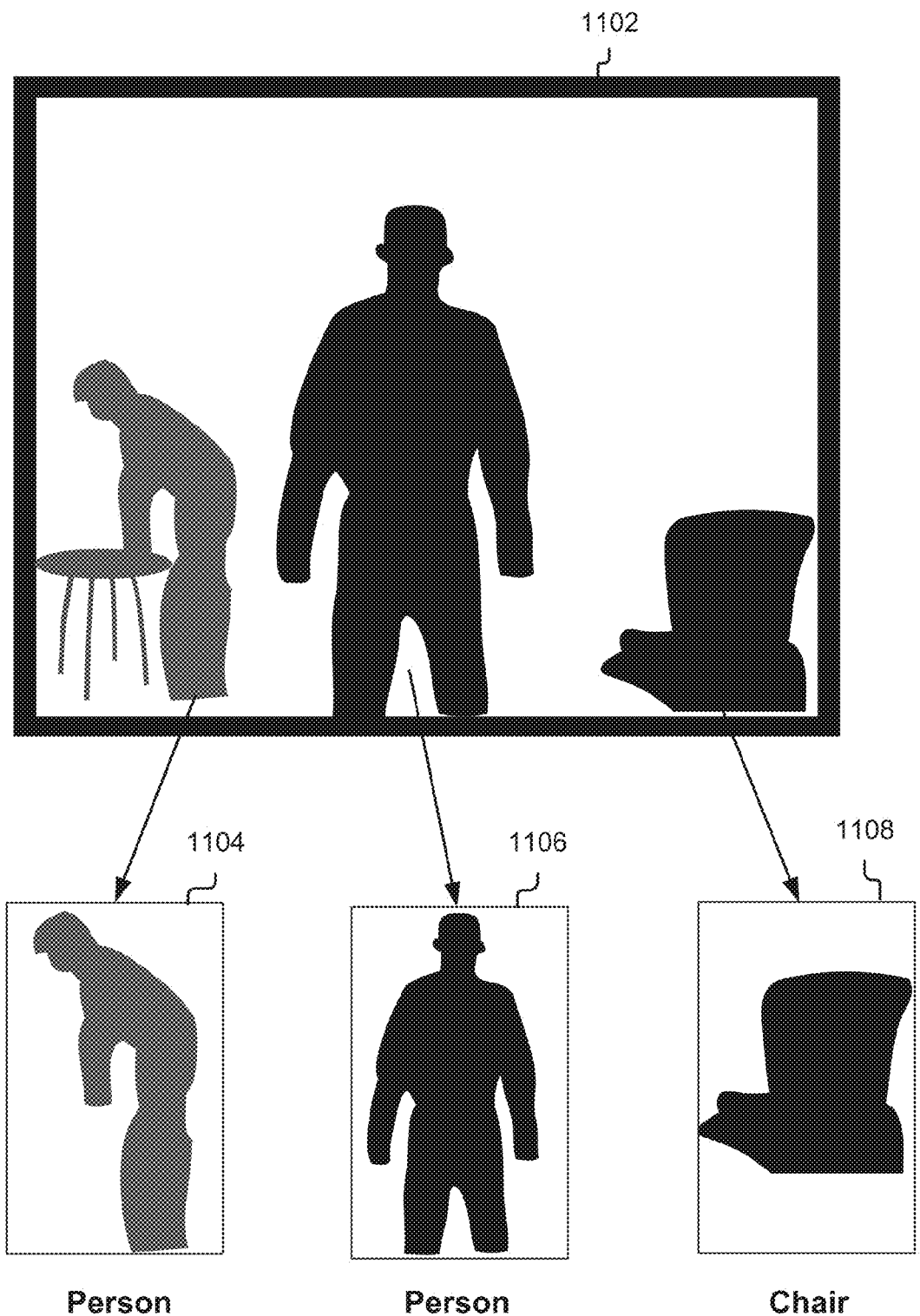
FIG. 11 is a graphical representation illustrating person detection from a depth image.

In some embodiments, the body pose estimation module 828 may detect people in in depth images using a layered approach. In this approach, the body pose estimation module 828 may search for connected components (e.g., blobs) in a depth image, and then identify segments (e.g., horizontal slices) of those blobs as belonging to people or other objects based on the curvature of the segments. For example, as depicted in FIG. 11, the body pose estimation module 828 can extract three blobs from a depth image 1102 and then identify each of the blobs as belonging to people 1104 and 1106 and a chair 1108.

The user's body pose (e.g., the user body position and/or orientation) identified by the body pose estimation module 828 can be used in various embodiments to identify head/arm positions and in combination with the speech recognition results to localize sound sources with speech, as described elsewhere herein.

Synchronization Layer 104

In the synchronization layer 104, the posterior likelihood estimator 832 (e.g., see FIG. 8C) may estimate posterior likelihoods of a sound source using various inputs from the detection layer 102 including from the sound source localization 108, the gesture detection 110, the speech recognition 112, and/or the body pose estimation 114. In some embodiments, a posterior likelihood may be estimated based on SSL, gesture, speech, and/or body pose. For instance, the posterior likelihood estimator 832 may estimate a posterior likelihood 116 (P($^\Phi$(x)|sound), where P($^\Phi$(x)) indicates a sound source of interest at a particular position x given a sound is detected. In some embodiments, the posterior likelihood estimator 832 may estimate the posterior likelihood 116 based on SSL performed by the sound source localization module 822, as discussed elsewhere herein. In some further embodiments, the posterior likelihood estimator 832 may combine the SSL with an output from the speech recognition component 112 to estimate the posterior likelihood 116 as indicated by signal line 138 and the dotted line leading to block 116 in FIG. 1.

Figure 4:
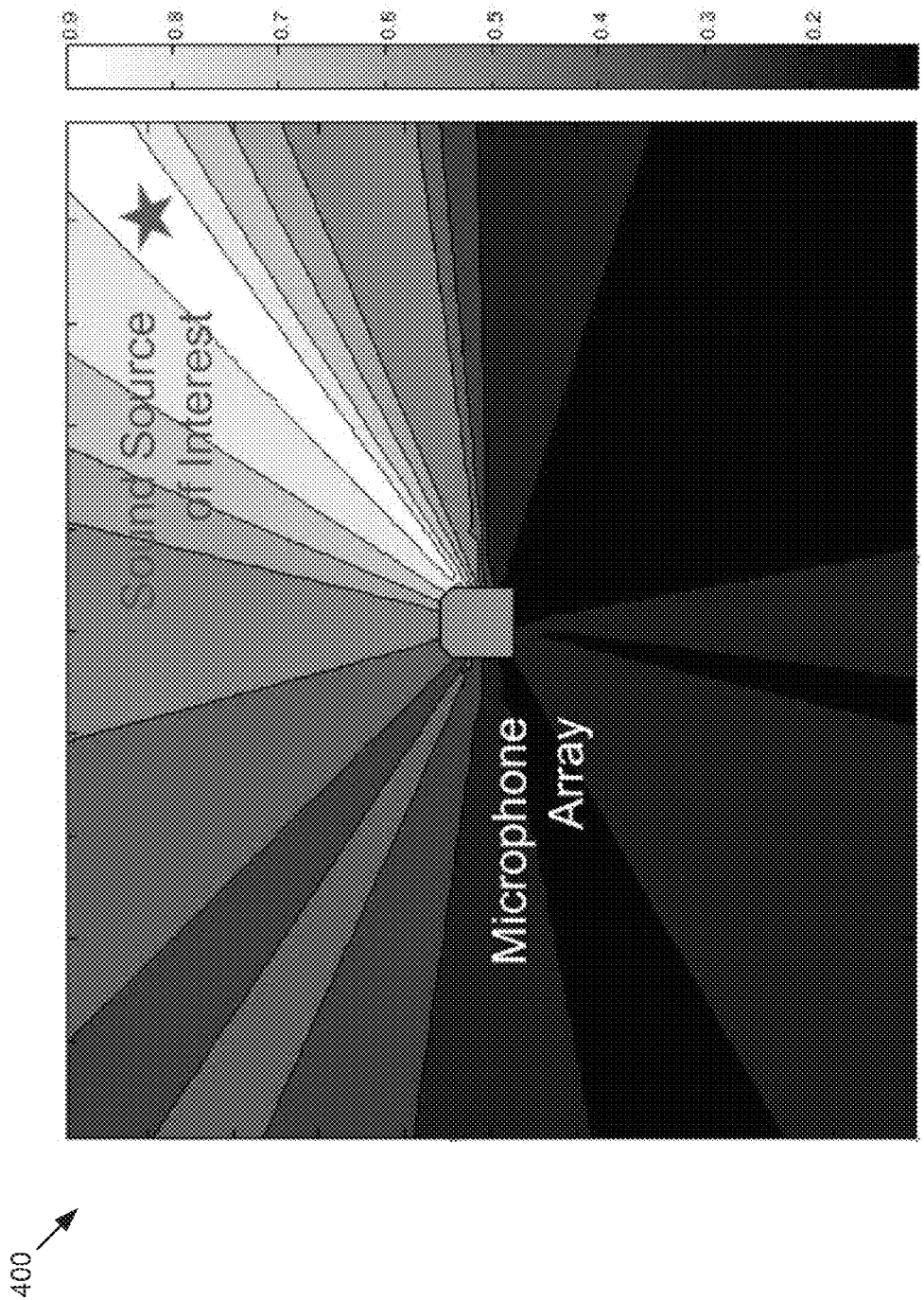
FIG. 4 is a graphical representation illustrating an example posterior likelihood estimate determined based on a set of time delay on arrival measurements from a microphone array.
Figure 12A:
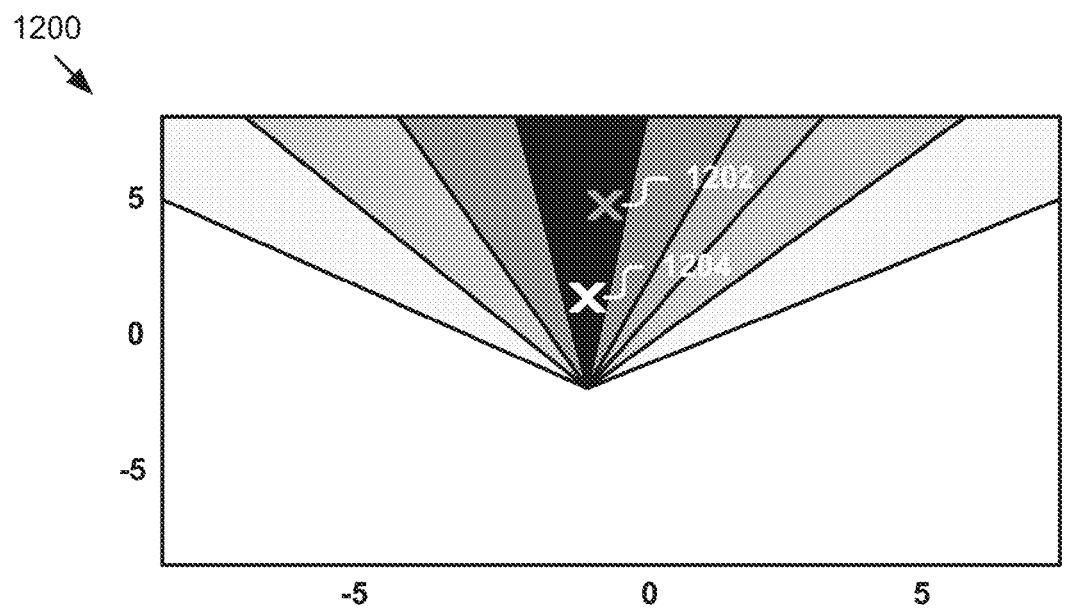
FIGS. 12A-12D are evidence grids representing posterior likelihoods estimated based on a user pointing direction, user speech, computational sound source localization, and a combination of the foregoing.
Figure 12B:
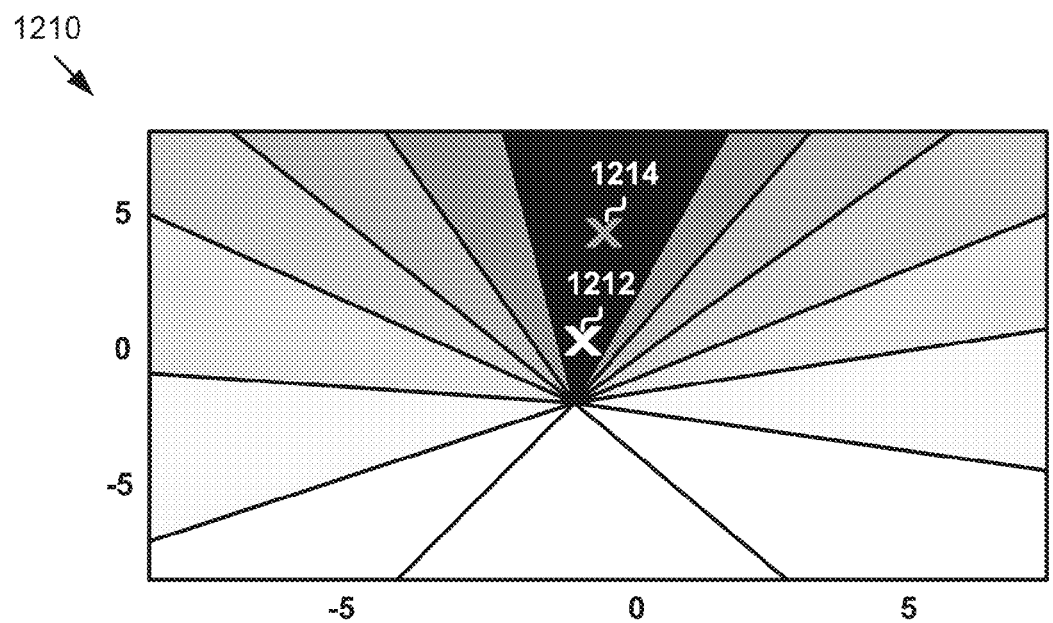
Figure 12C:
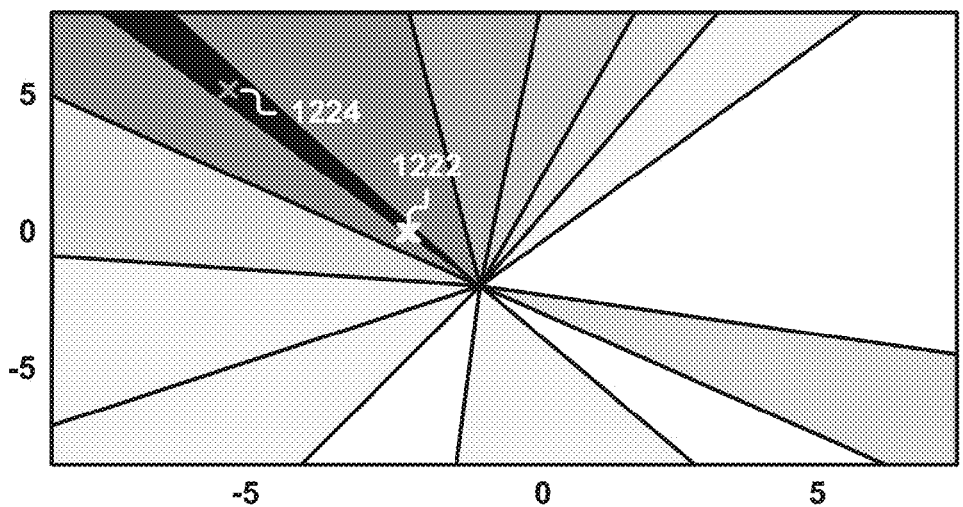

The posterior likelihood estimator 832 may provide the posterior likelihood estimate 116 to the graphical representation module 834 (e.g., see FIG. 8B) for it to generate an evidence grid representing the estimate. For example, FIG. 12C depicts an evidence grid 1220 representing a posterior likelihood of a sound source estimated based on SSL. In the evidence grid 1220, the black region indicates a highly likely sound source region while the white region indicates an unlikely sound source region. The white cross as indicated by reference numeral 1222 is used to indicate the actual sound source position while the grey cross as indicated by reference numeral 1224 is used to indicate an estimated position based on the posterior likelihood represented by the grid 1220. By way of another example, FIG. 4 is a graphical representation illustrating a posterior likelihood estimate based on a set of time delay on arrival measurements from a capturing device (e.g., microphone array).

The posterior likelihood estimator 832 may estimate a posterior likelihood 118 (P($^\Phi$(x)|gesture), where P($^\Phi$(x)) indicates a sound source of interest at a particular position x given a user gesture, such as a pointing direction is detected. In some embodiments, the posterior likelihood estimator 832 may estimate the posterior likelihood 118 based on a user pointing direction and/or gesture identified by the gesture detection module 824, as discussed elsewhere herein. In some further embodiments, the posterior likelihood estimator 832 may combine the user gesture (e.g., gesturing direction) with a user's body pose (e.g., the user's body position and/or orientation) to estimate the posterior likelihood 118 as indicated by signal lines 130 and 132 in FIG. 1.

Figure 5:
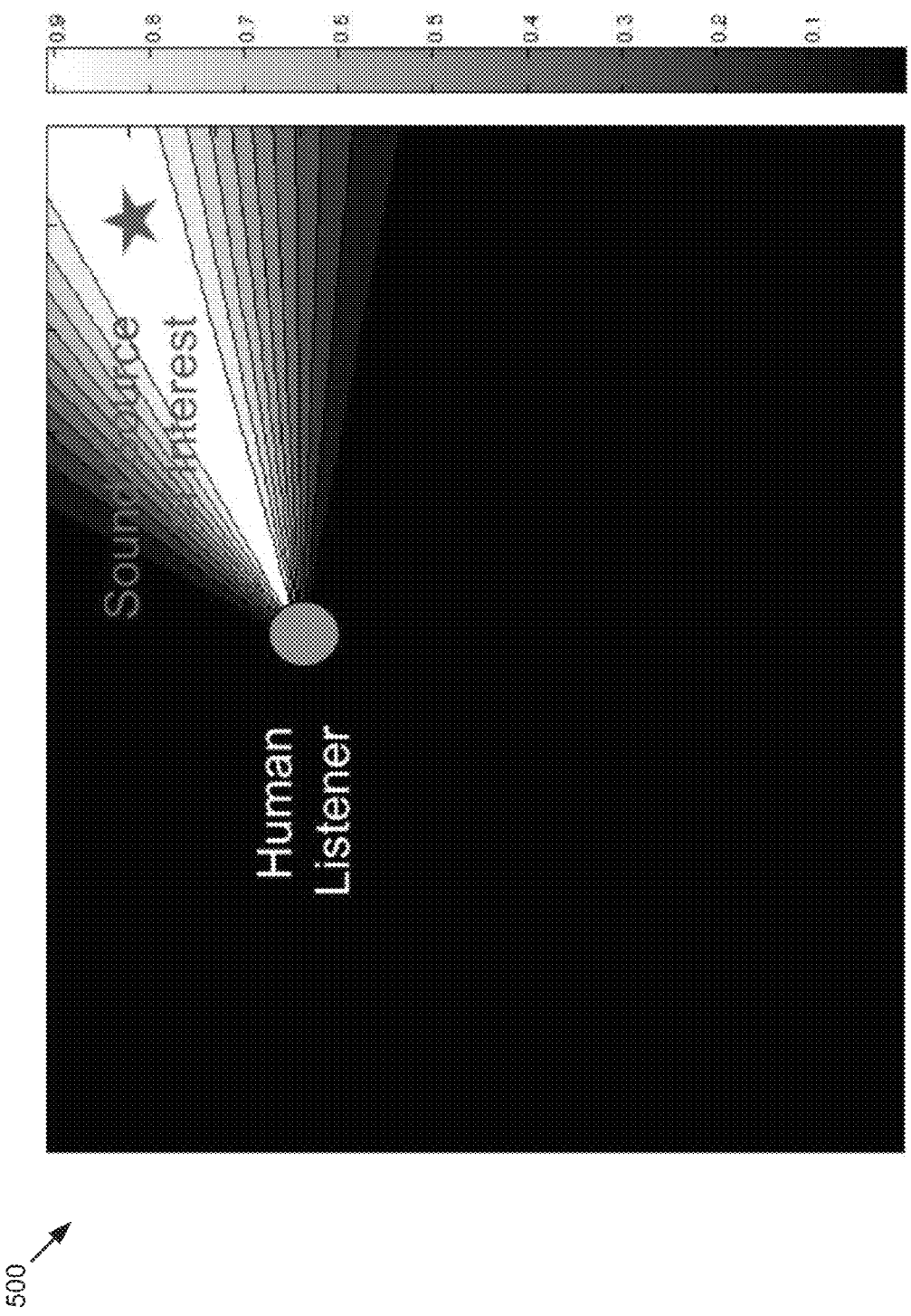
FIG. 5 is a graphical representation illustrating an example posterior likelihood estimate determined based on a user pointing gesture.

The posterior likelihood estimator 832 may provide the posterior likelihood estimate 118 to the graphical representation module 834 for it to generate an evidence grid representing the estimate. For example, FIG. 12A depicts an evidence grid 1200 representing a posterior likelihood of a sound source estimated based on a user pointing gesture. In the evidence grid 1200, the black region indicates a highly likely sound source region while the white region indicates an unlikely sound source region. The white cross as indicated by reference numeral 1204 is used to indicate the actual sound source position while the grey cross as indicated by reference numeral 1202 is used to indicate an estimated position based on the posterior likelihood represented by the grid 1200. By way of another example, FIG. 5 is a graphical representation depicting a posterior likelihood estimate of a sound source based on a user pointing direction.

The posterior likelihood estimator 832 may estimate a posterior likelihood 120 (P($^\Phi$(x)|speech), where P($^\Phi$(x)) indicates a sound source of interest at a particular position x given a user speech is detected. In some embodiments, the posterior likelihood estimator 832 may estimate the posterior likelihood 120 based on a user speech segment recognized by the speech recognition module 826, as discussed elsewhere herein. In further embodiments, the posterior likelihood estimator 832 may combine the user speech with a user's body pose (e.g., the user's body position and/or orientation) to estimate the posterior likelihood 120 as indicated by signal lines 134 and 136 in FIG. 1.

Figure 6:
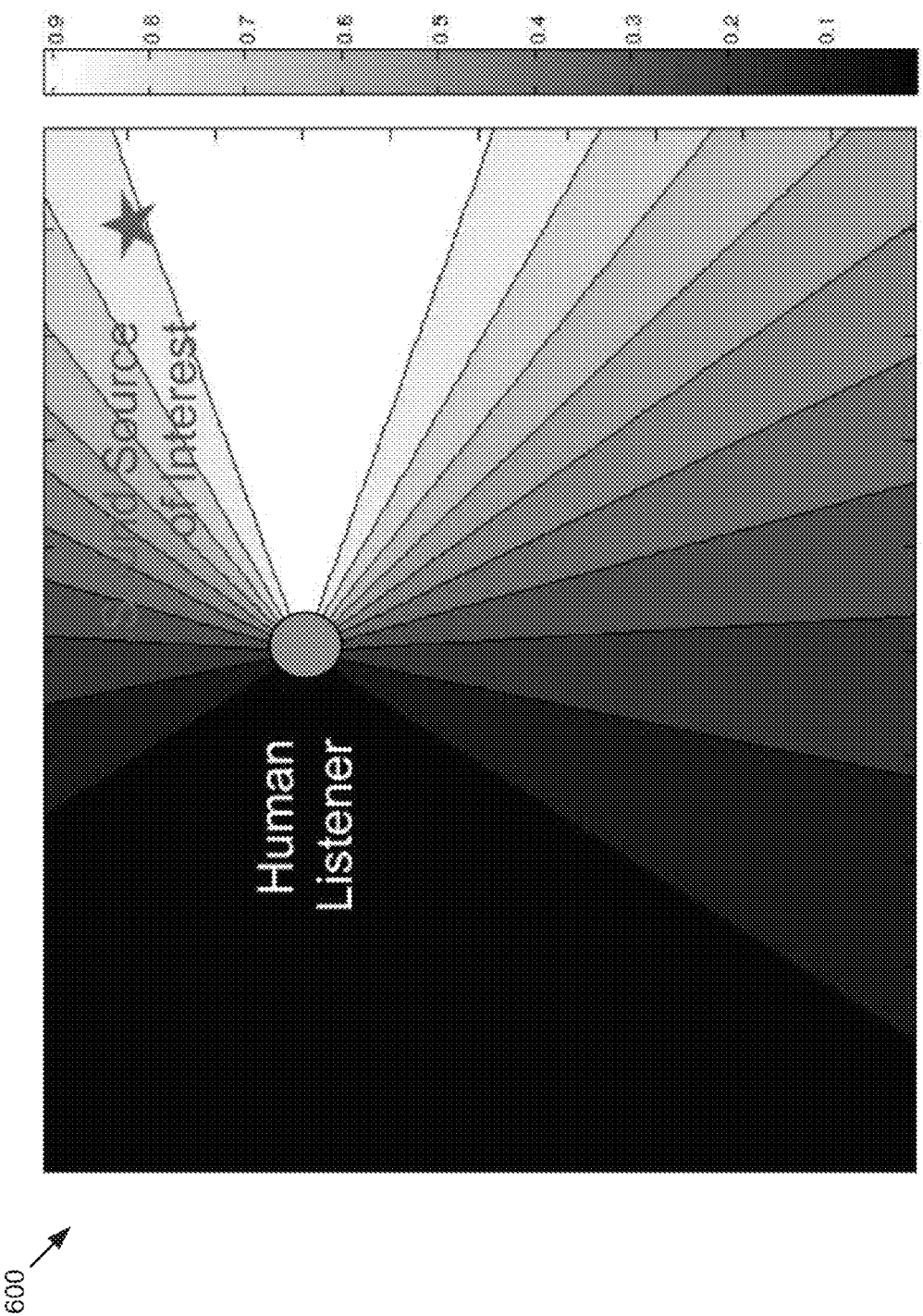
FIG. 6 is a graphical representation illustrating an example posterior likelihood estimate determined based on a user speech segment.

The posterior likelihood estimator 832 may provide the posterior likelihood estimate 120 to the graphical representation module 834 for it to generate an evidence grid representing the estimate. For example, FIG. 12B depicts an evidence grid 1210 representing the posterior likelihood of the sound source estimated based on a user speech. In the evidence grid 1210, the black region indicates a highly likely sound source region while the white region indicates an unlikely sound source region. The white cross as indicated by reference numeral 1212 is used to indicate the actual sound source position while the grey cross as indicated by reference numeral 1214 is used to indicate an estimated position based on the posterior likelihood represented by the grid 1210. By way of another example, FIG. 6 is a graphical representation depicting a posterior likelihood estimate of a sound source based on a user speech command indicating the direction "right". It should be understood that one or more combinations as discussed above for estimating the posterior likelihood 116, 118, and 120 are not limiting, and other combinations are also possible including, for example, estimating the posterior likelihood 118 based on combining outputs from the gesture detection 110, speech recognition 112, and body pose estimation 114 components, respectively.

In some embodiments, given a point of origin and an angle, Θ, the posterior likelihood estimator 832 may estimate a likelihood, L, using the following equation:

$$L(d\theta, \sigma) = K_1 e^{-0.5*(d\theta/\sigma)^2} + K_0,$$

where dθ is the angular distance from an arbitrary point in space to the ray centered in the body, σ represents the standard deviation in pointing gesture accuracy, and $K_1$ and $K_0$ are constants limiting the range of maximum likelihood.

Fusion Layer 106

In the fusion layer 106, the fusion module 842 (e.g., see FIG. 8D) may fuse posterior likelihood estimated in the synchronization layer 104 into an overall posterior likelihood 122. In some embodiments, the fusion module 842 fuses the estimated posterior likelihoods by combining them together. In a further example, the fusion module 842 may first add the posterior likelihoods estimated based on user inputs (e.g., user gesture, user speech, user body pose, etc.) together into a combined posterior likelihood, scale or normalize the combined posterior likelihood to come in same range of the posterior likelihood estimated based on sound source location (SSL), and then add the scaled/normalized combined posterior likelihood to the posterior likelihood associated with SSL to estimate an overall posterior likelihood.

In some embodiments, the fusion module 842 may be directly coupled to the posterior likelihood estimator 832 to receive the posterior likelihoods 116, 118, and/or 120 and then combine them to determine the overall posterior likelihood 122. The overall posterior likelihood 122 (P(Φ(x)|sound, gesture, speech) may indicate an actual position 124 of the sound source of interest based on combining the posterior likelihoods estimated based on the sound source location (SSL), the user gesture, and/or the user speech.

Figure 12D:
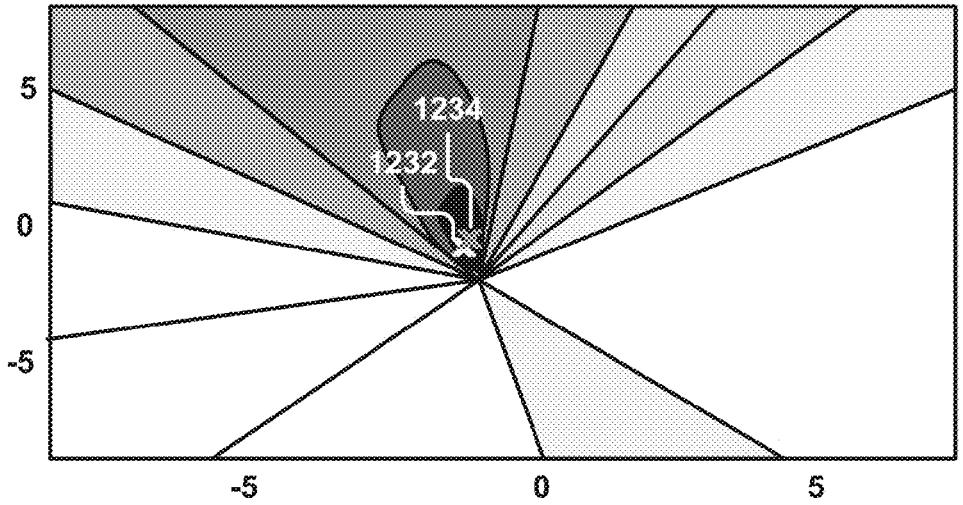

In some embodiments, the fusion module 842 may provide the overall posterior likelihood 122 to the graphical representation module 834 for it to generate an evidence grid representing the overall likelihood. For example, FIG. 12D depicts an overall evidence grid 1230 representing the overall posterior likelihood of the sound source estimated based on combining likelihoods associated with a user pointing gesture, user speech, and SSL. In this figure, the angles generated from user inputs and the SSL, when combined, effectively triangulate upon the source location. As shown, a small region of high likelihood is centered about the real source location. In some embodiments, the graphical representation module 834 may combine the evidence grids 1200, 1210, and 1220 to generate the overall evidence grid 1230. In some embodiments, prior to combining, each evidence grid may first be scaled and/or normalized to a same range (because of different sampling rates associated with SSL 108, gesture detection 110, speech recognition 112, etc.) and once each evidence grid is scaled to the same range, they may be combined together to generate the overall evidence grid 1230. Ideally, fusing evidence grids created by the separate In some embodiments, posterior likelihoods and/or evidence grids are combined or fused by adding, averaging, or otherwise mathematically compiling them together. However, in some embodiments, substantially different sampling rates may be used to detect inputs, and as a result, each grid may be normalized to the same range before they are fused together. For instance, each grid may be scaled to within [−3, 3] before they are combined together. In some embodiments, sound source locations may be extracted from the grid by thresholding the evidence grade, which may leave regions of high likelihood. These regions are then clustered to find the target location. As an example, in a scenario having one real sound source, the weighted centroid of the cluster with the greatest cumulative evidence may be selected as the target location.

Figure 7:
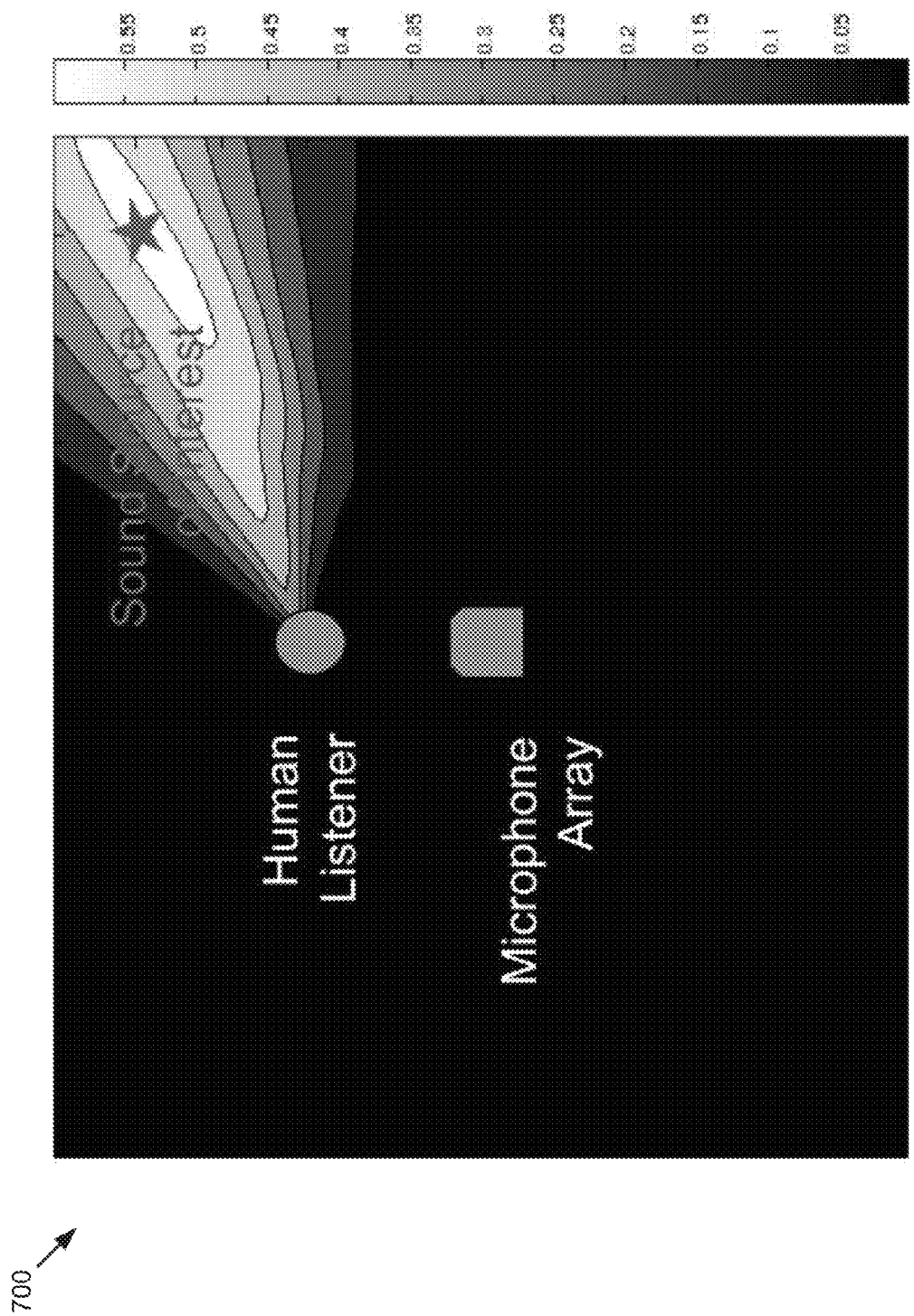
FIG. 7 is a graphical representation illustrating an example posterior likelihood estimate determined based on the combination of computational sound source localization and one or more user inputs.

In the evidence grid 1230, the rounded black region indicates a highly likely sound source region while the white region indicates an unlikely sound source region. The white cross as indicated by reference numeral 1232 is used to indicate the actual sound source position while the grey cross as indicated by reference numeral 1234 is used to indicate an estimated position based on the overall posterior likelihood represented by the grid 1230. As depicted, the overall posterior likelihood as represented by the grid 1230 is representative of an actual position that approximates the real position of the sound source. As an another example, FIG. 7 depicts a graphical representation of an overall posterior likelihood estimate of a sound source based on combining the SSL and user inputs.

In some embodiments, the overall posterior likelihood 122 and the overall evidence grid representing the overall posterior likelihood 122 can be passed on to the sound source investigator 844 (e.g., see FIG. 8D) for further sound source analysis. In some embodiments, the overall evidence grid includes a narrowed auditory space (e.g., see FIG. 12D) as compared to the original auditory space before estimating the overall posterior likelihood (e.g., see FIGS. 12A-C), and the sound source investigator 844 may use this narrowed auditory space for investigating other objects of interest. In some embodiments, the sound source investigator 844 may use one or more perceptual object investigation algorithms 126 for performing this investigation. Performing further analysis or investigation on the narrowed auditory space is advantageous because (1) false positives may be reduced as search space is significantly narrowed, (2) processing may be reduced with the size of the search space, and (3) it does not overwhelm the user with uninteresting directions and the need to search the entire surrounding space.

Methods

Figure 2:
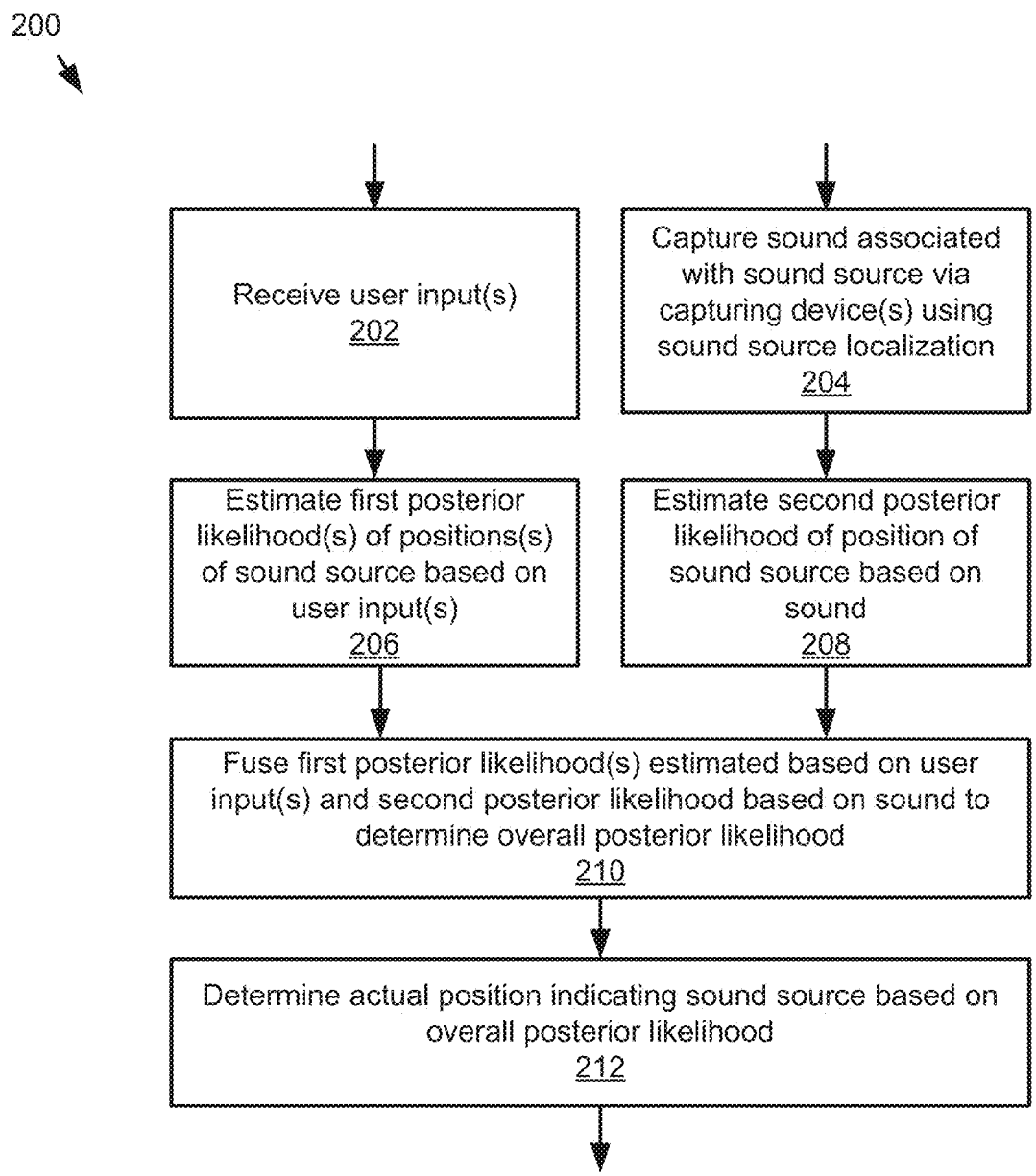
FIG. 2 is a flowchart of an example method for determining a position of a sound source of interest based on sound source localization and user inputs.
Figure 8A:
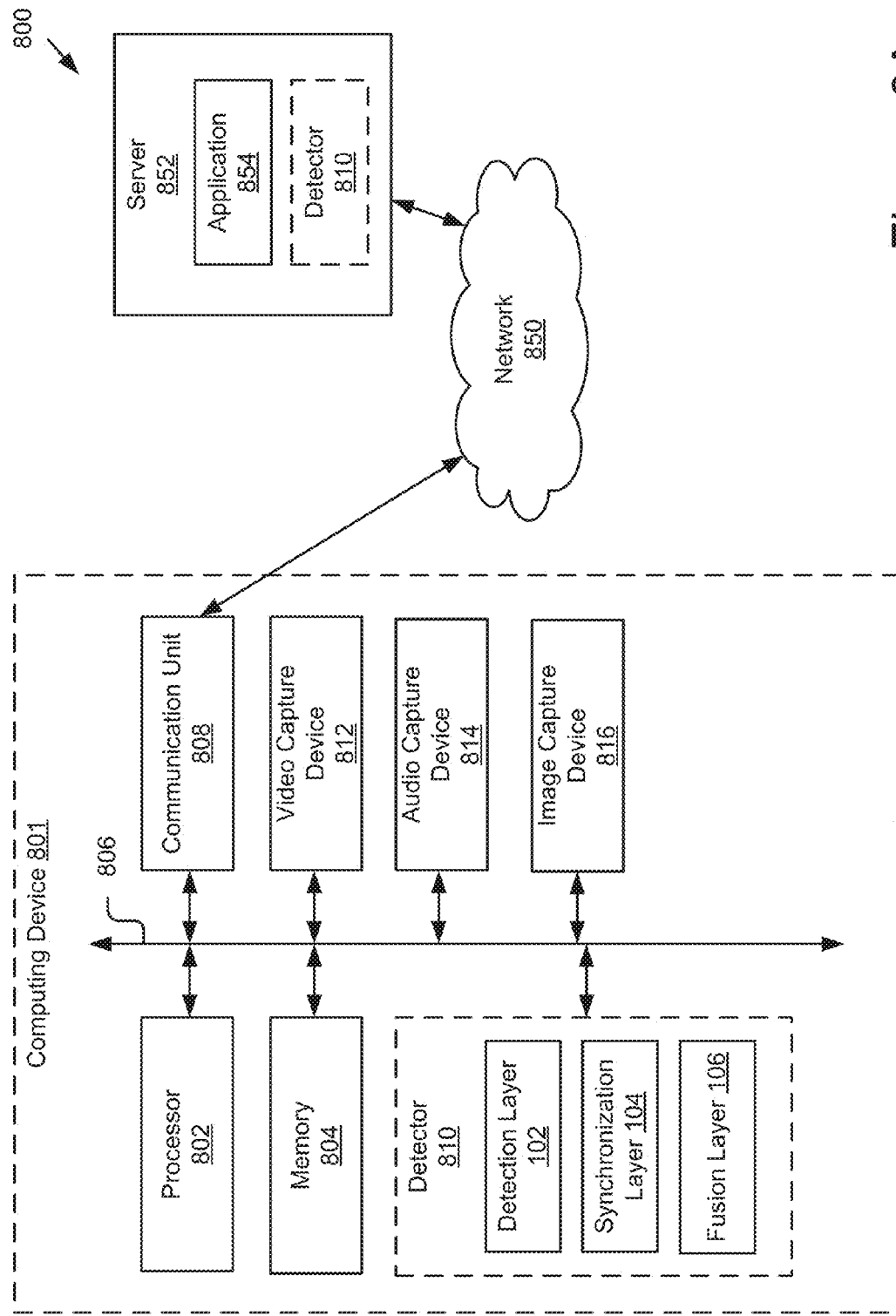
FIG. 8A is a block diagram illustrating an example system architecture.

FIG. 2 is a flowchart of an example method 200 for determining a position of a sound source of interest based on SSL and user inputs. In block 202, one or more user inputs are received. In some embodiments, the one or more user inputs may include one or more of a user gesture, a user speech segment, and/or a user body pose, which may be detected by the gesture detection module 824, the speech recognition module 826, and/or the body pose estimation module 828, respectively. In block 204, one or more capturing devices may capture a sound associated with a sound source using SSL. A capturing device may include a microphone array, such as a video capture device (e.g., the video capture device 812), an audio capture device (e.g., the audio capture device 814), or an image capturing device (e.g., the image capture device 816), as depicted in FIG. 8A.

Upon receiving the one or more user inputs in block 202 and the localized sound in block 204, the posterior likelihood estimator 832 may estimate 206 one or more first posterior likelihoods of one or more positions of the sound source based on the one or more user inputs and estimate 208 a second posterior likelihood of a position of the sound source based on the sound. In some embodiments, the posterior likelihood estimator 832 may provide the one or more first posterior likelihoods and the second posterior likelihood to the fusion module 842 for it to perform its acts and/or functionalities thereon.

The fusion module 842 may fuse 210 the one or more first posterior likelihoods estimated based on the one or more user inputs and the second posterior likelihood estimated based on the sound to determine an overall posterior likelihood. In block 212, an estimate for an actual position of the sound source may be determined based on the overall posterior likelihood, as described elsewhere herein. In some embodiments, the operation in block 212 may be performed by the sound source investigator 844.

Figure 8B:
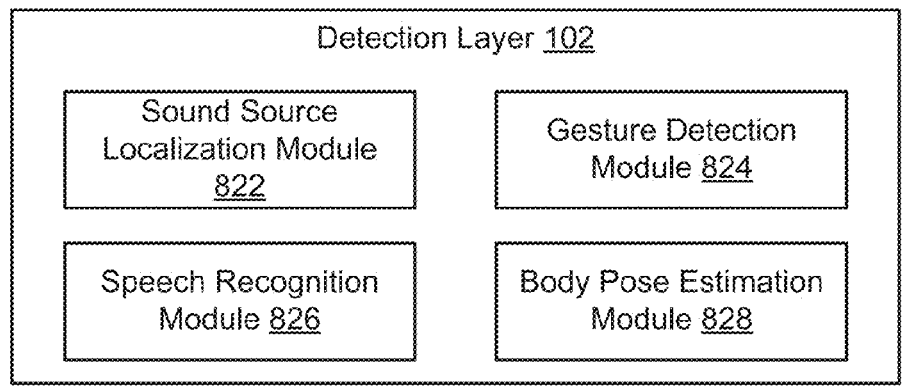
FIG. 8B is a block diagram of an example detection layer.

FIG. 3A-3E is a flowchart of an example method 300 for determining a position of a sound source of interest based on two or more inputs. In block 302, one or more inputs are detected. The one or more inputs may be detected as one or more sound source locations (as shown in block 304), a user body pose (as shown in block 306), a user gesture (as shown in block 308), and/or a user speech segment (as shown in block 310). In some embodiments, the one or more inputs may be detected by one or more software and/or hardware components of the detection layer 102 as shown in FIG. 8B. For instance, the one or more sound source locations may be detected by the sound source localization module 822, the gesture may be detected by the gesture detection module 824, the speech segment may be detected by the speech recognition module 826, and/or the user body pose may be detected by the body pose estimation module 828, etc.

Figure 3A:
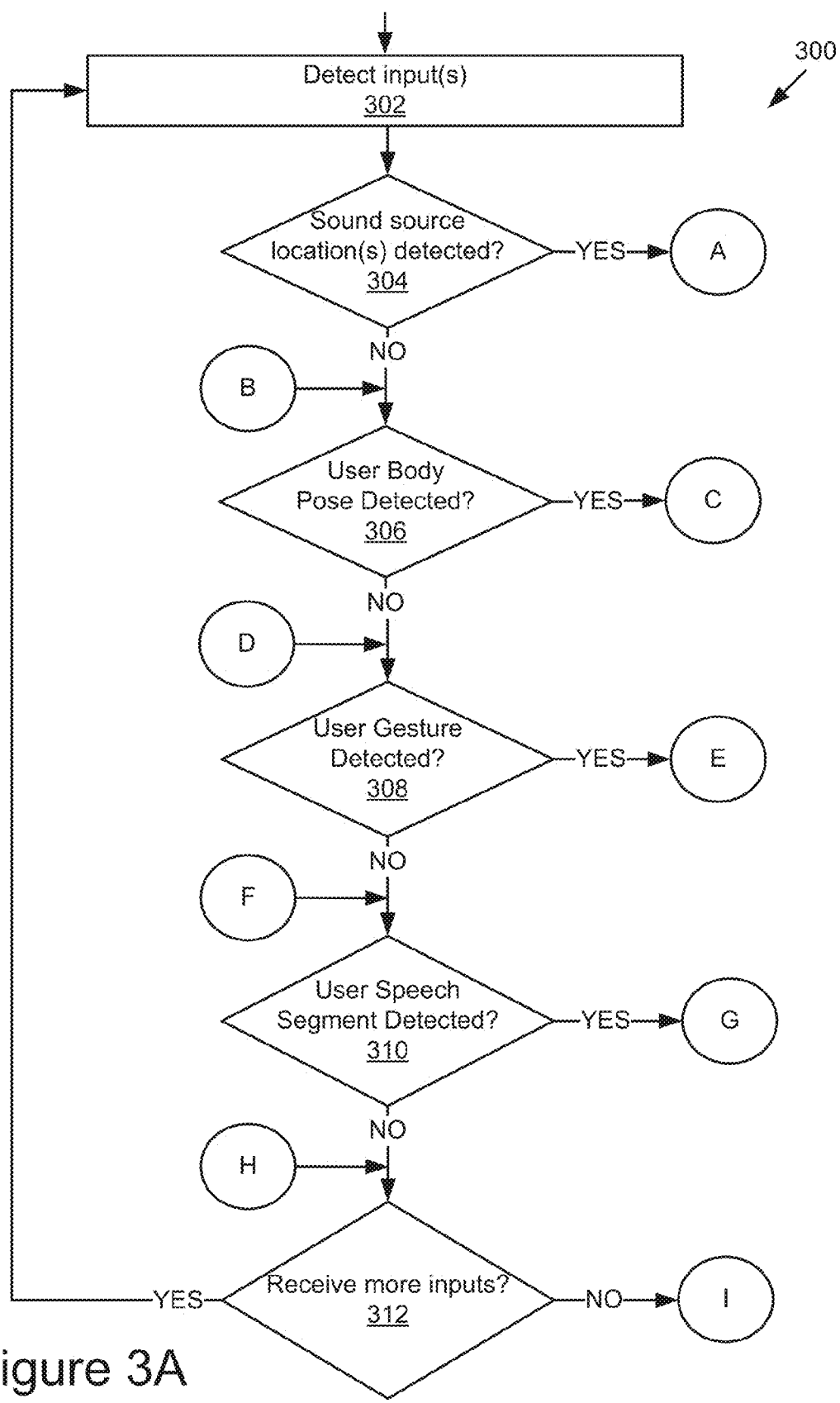
FIG. 3A-3G are flowcharts of example methods for determining a position of a sound source of interest based on sound source localization and various user inputs.
Figure 3B:
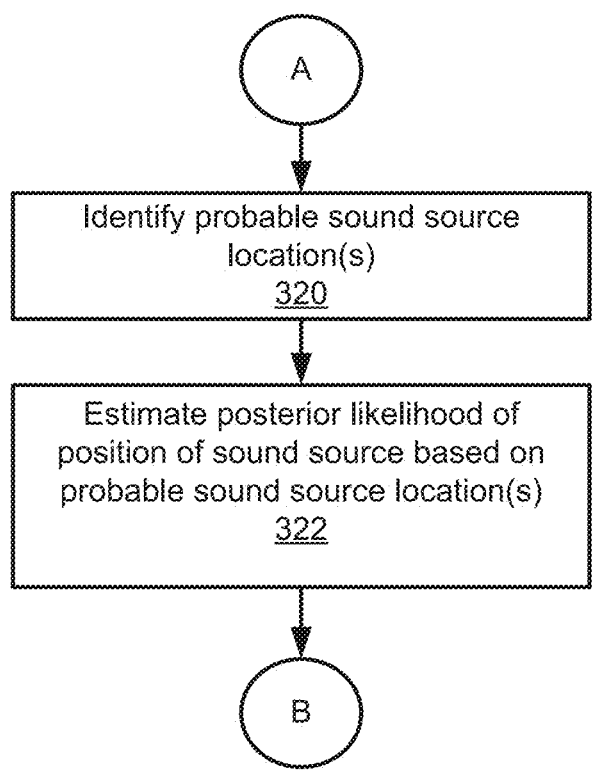
Figure 3C:
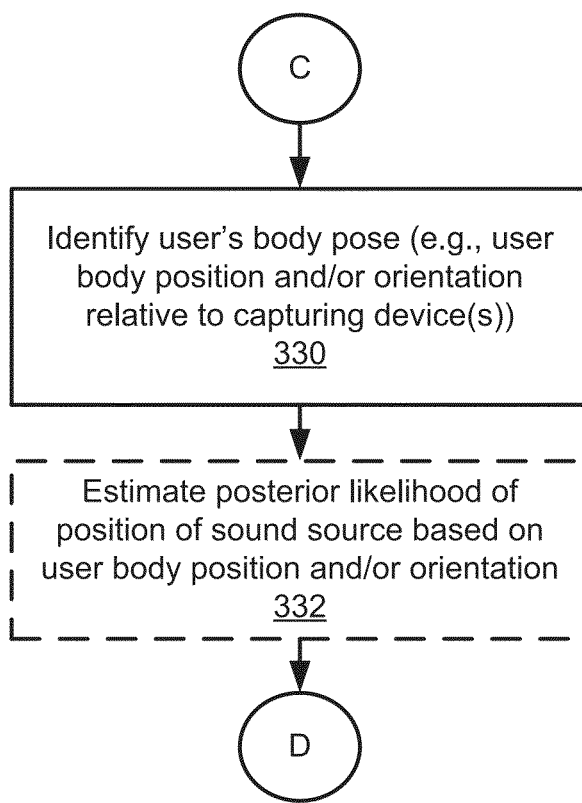
Figure 3D:
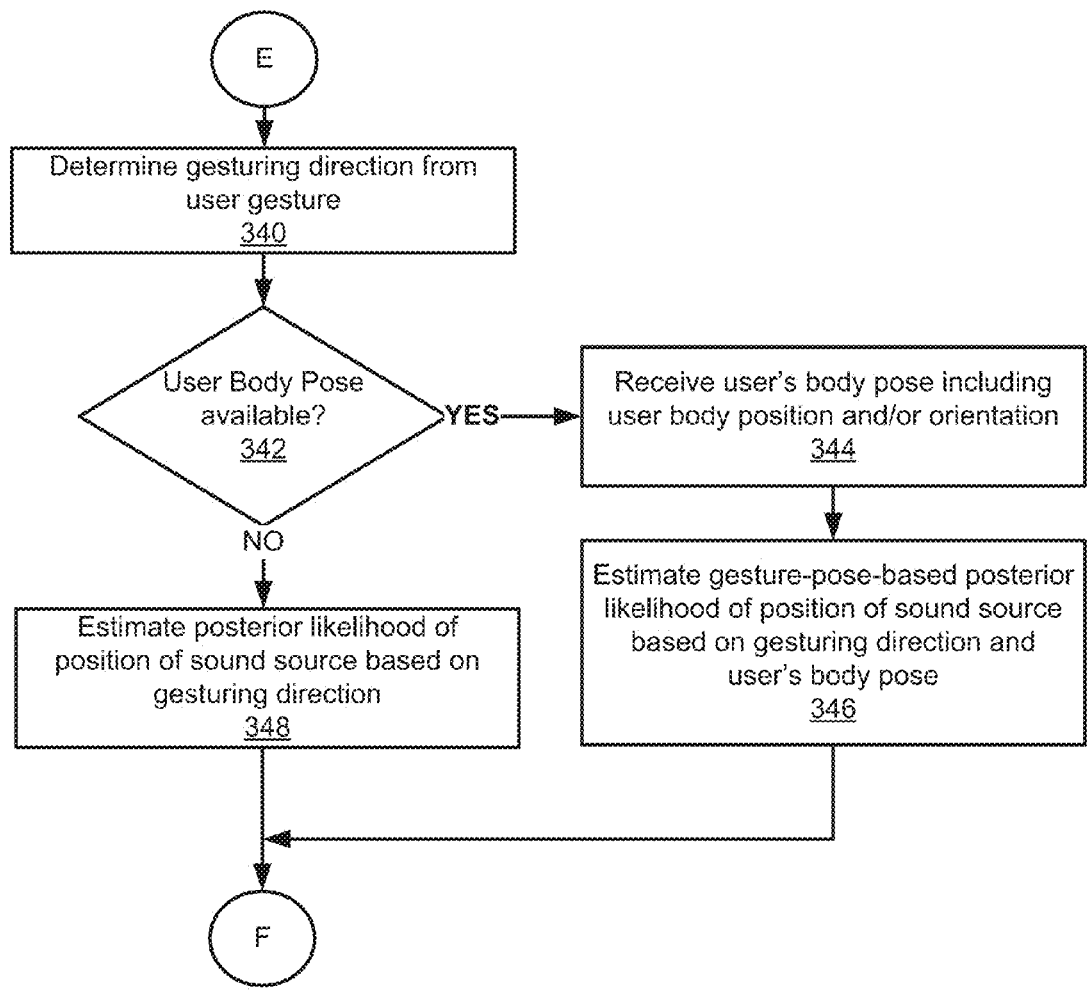
Figure 3E:
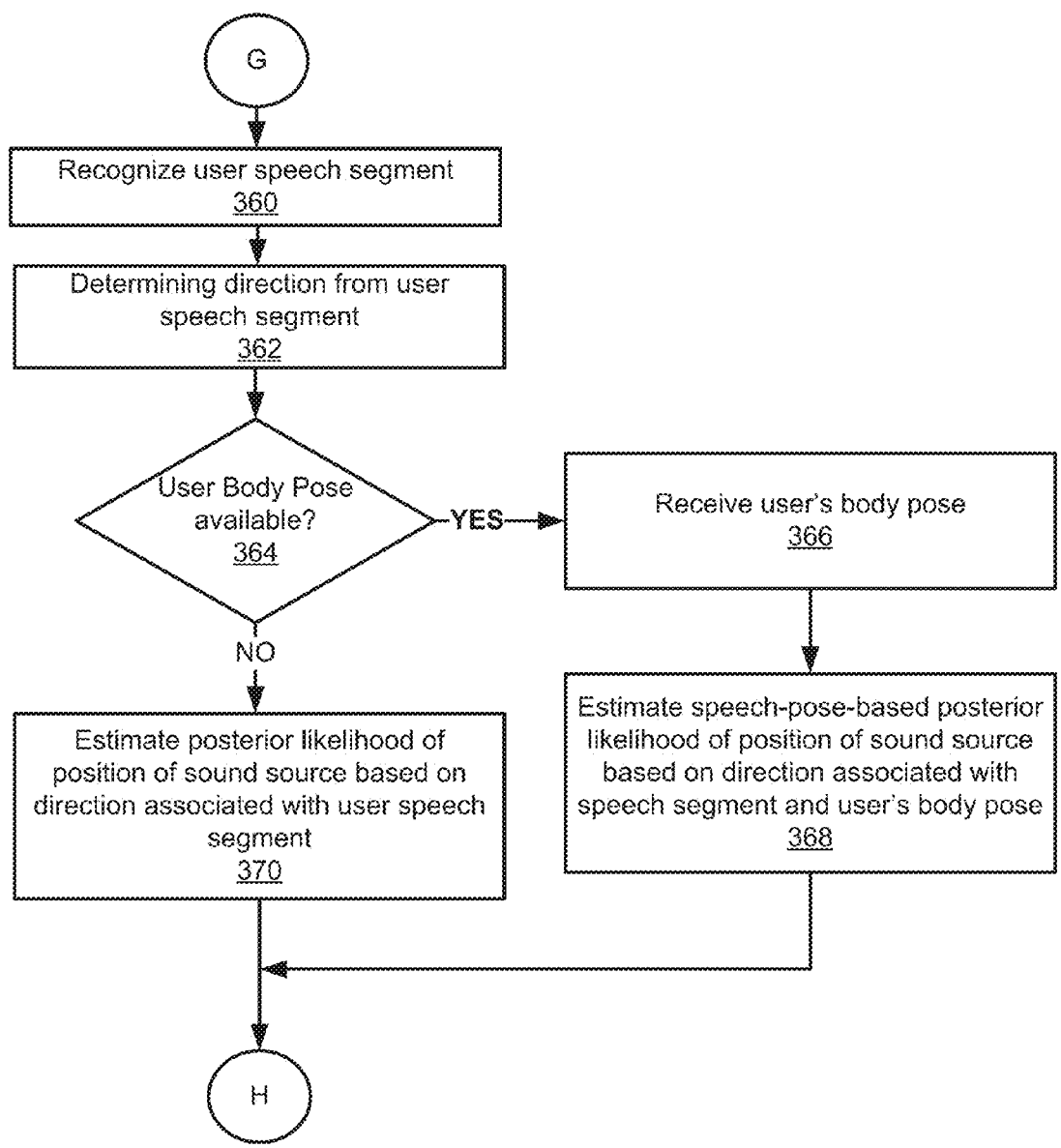
Figure 3F:
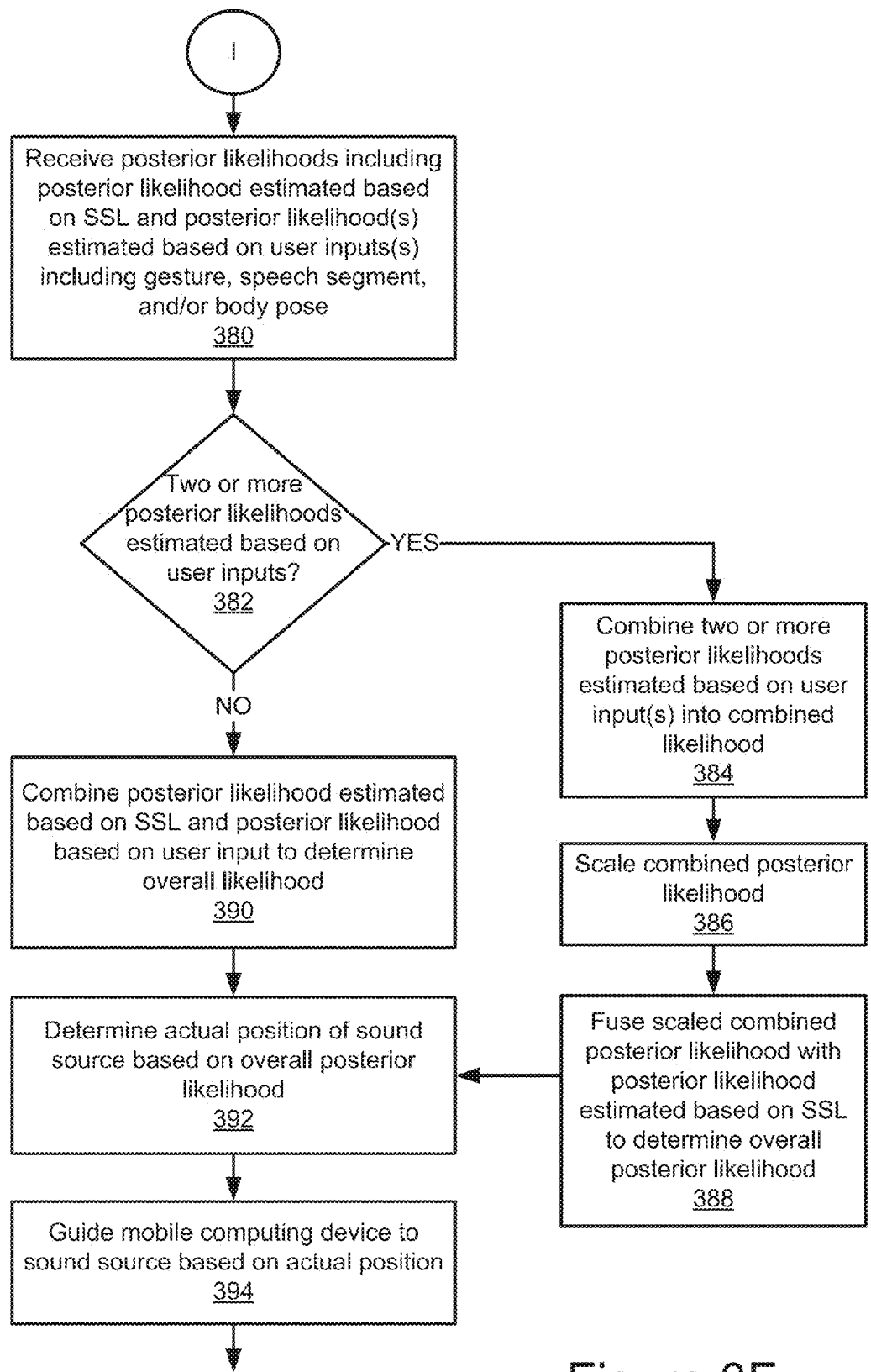
Figure 3G:
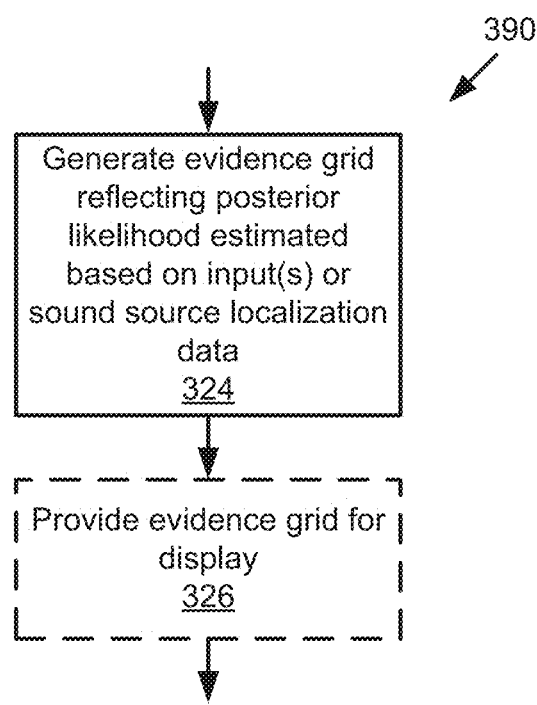

If in block 304, one or more sound source locations are detected then the sound source localization module 822 may identify 320 one or more probable sound source locations and provide them to the posterior likelihood estimator 832, which may use them to estimate 322 a posterior likelihood of a position of the sound source. In some embodiments, the posterior likelihood estimator 832 may generate an evidence grid that graphically represents the posterior likelihood of a position of a sound source (e.g., see FIGS. 12A-D) based on the one or more probable sound source locations. For instance, as shown in the method 390 of FIG. 3G, the graphical representation module, in cooperation with the posterior likelihood estimator 832, may generate 330 an evidence grid that graphically represents the posterior likelihood of a position of a sound source based on various inputs, such as one or more user inputs or sound source localization data. In various cases, the evidence grid may be provided for display 326 by the detector 810.

Returning to FIG. 3A, if in block 306, a user body pose is detected then the body pose estimation module 828 may identify 330 the user's body pose. In some embodiments, a body pose may include the user's body position and/or orientation relative to one or more capturing devices). In some embodiments, the body pose may be used with other inputs to generate various posterior likelihood estimates, as discussed elsewhere herein. In other embodiments, the body pose may be provided to the posterior likelihood estimator 832, which may use it to estimate 332 a posterior likelihood of a position of the sound source. In some embodiments, the graphical representation module 834 may generate an evidence grid reflecting the posterior likelihood estimated based on the user's body pose, as discussed elsewhere herein.

If in block 308, a user gesture is detected then the gesture detection module 824 may identify 340 a direction in which the user is gesturing (e.g., pointing) and then provide the gesturing direction to the posterior likelihood estimator 832 to estimate a posterior likelihood. In block 342, the body pose estimation module 828 determines whether a user's body pose is available, and if so, the posterior likelihood estimator 832 receives 344 the user body pose including the user body position and/or orientation from the body pose estimation module 828 and/or a memory and estimates 346 a gesture-pose-based posterior likelihood of a position of the sound source based on a combination of gesturing direction and the user's body pose. If the determination in block 342 is negative, then the posterior likelihood estimator 832 may estimate 348 a posterior likelihood of a position of the sound source based on the gesturing direction. In some embodiments, the graphical representation module 834 may generate an evidence grid reflecting the gesture-based posterior likelihood and/or the gesture-pose-based posterior likelihood, as discussed elsewhere herein.

If in block 310, a user speech segment is detected then the speech recognition module 826 may recognize 360 the user speech segment and determine 362 a direction from the speech segment. For example, a user has asked about a particular sound by using a speech segment "what's that sound on the right?" and the speech recognition module 826 may recognize this speech segment and determine the direction "right" from the segment. In block 364, a determination is made as whether user body pose is available. If the result of the determination is affirmative, then the posterior likelihood estimator 832 may receive 366 the user's body pose and estimate 368 a speech-pose-based posterior likelihood of a position of the sound source based on a combination of a direction associated with the user speech segment and the user's body pose. If on the other hand the result of the determination in block 342 is negative, then the posterior likelihood estimator 832 may estimate 370 a posterior likelihood of a position of the sound source based on the direction associated with the user speech segment. In some embodiments, the graphical representation module 834 may generate an evidence grid reflecting the speech-based posterior likelihood and/or the speech-pose-based posterior likelihood, as discussed elsewhere herein.

Next, then the method 300 may determine whether to receive 312 more inputs. If the result of the determination in block 312 is affirmative, then the method 300 may return to block 302 to detect additional inputs. Otherwise, the method 300 continues to block 380 where the fusion module 842 may receive, from the posterior likelihood estimator 832, the posterior likelihood estimated based on the one or more probable sound source location and one or more posterior likelihoods estimated based on one or more user inputs including the user gesture, the user speech segment, and/or the user body pose.

In some embodiments, a determination is made in block 382 as whether two or more posterior likelihoods are estimated based on two or more user inputs. If the result of the determination in block 382 is affirmative, then the fusion module 842 may combine 384 the two or more posterior likelihoods into a combined posterior likelihood, scale and/or normalize 386 the combined posterior likelihood, and then fuse 388 the scaled combined posterior likelihood and the posterior likelihood estimated based on SSL to determine an overall posterior likelihood. If on the other hand, the result of the determination in block 382 is negative, then the fusion module 842 may combine 390 the posterior likelihood estimated based on the SSL and a posterior likelihood estimated based on the relevant user input to determine an overall posterior likelihood. In block 392, an estimation of the actual position of the sound source is determined based on the overall posterior likelihood. In some embodiments, the estimation of the actual position may be determined by determining a position that maximizes the overall posterior likelihood. The estimated actual position may then be used to guide 394 a mobile computing device (e.g., robot) to the sound source.

System Architecture

As depicted in FIG. 8A, the technology described herein may include a system 800 having a computing device 801. The system 800 also includes a server 852 hosting an application 854. Each of the entities 801 and/or 852 may be coupled to a network 850 for cooperation and electronic communication with one another. The architecture illustrated in FIG. 8A is provided by way of non-limiting example and it should be understood that numerous other configurations are possible and contemplated. For example, any number of computing devices 801 and/or servers 852 may be included in the system 800 and coupled to the network 850.

The network 850 can be a conventional type, wired or wireless, and may have numerous different configurations including a star configuration, token ring configuration, or other configurations. Furthermore, the network 850 may include one or more local area networks (LAN), wide area networks (WAN) (e.g., the Internet), public networks, private networks, virtual networks, and/or other interconnected data paths across which multiple devices may communicate. In some embodiments, the network 850 may be a peer-to-peer network. The network 850 may also be coupled to or includes portions of a telecommunications network for sending data in a variety of different communication protocols. In some embodiments, the network 850 includes Bluetooth communication networks or a cellular communications network for sending and receiving data including via short messaging service (SMS), multimedia messaging service (MMS), hypertext transfer protocol (HTTP), direct data connection, WAP, email, etc. Although FIG. 1 illustrates one network 850 coupled to the computing device 801 and the server 852, in practice one or more networks 850 can be connected to these entities.

The computing device 801 is any device having data processing and communication capabilities. The computing device 801 may couple to and communicate with one another and the other entities of the system 800 via the network 850 using a wireless and/or wired connection. As depicted in FIG. 8A, the computing device 801 may include a processor 802, a memory 804, a communication unit 808, a detector 810, a video capture device 812, an audio capture device 814, an image capture device 816, and a communication bus 806 that couples its constituent hardware components for communication/signaling purposes. However, it should be understood that the computing device 801 is not limited to the components illustrated in the computing device 801, and may include one or more other components including for example, a power source (e.g., battery), a GPS receiver; a Bluetooth® module, sensors (e.g., accelerometers, gyroscopes, thermocouples), graphics processor, firmware, operating systems for managing the hardware and resources of the computing device 801, drivers, various physical connection interfaces (e.g., USB, HDMI, etc.), etc. Non-limiting examples of a computing device 801 include a robot, smartphone, a tablet computer, a laptop computer, a netbook computer, a desktop computer (e.g., equipped with a touchscreen), a vehicle with an on-board computing device, a computing surface (e.g., a computer-enabled countertop, a tabletop, a wall, etc.), and/or any other computing devices capable of providing similar acts and/or functionality.

The processor 802 can include one or more processing units, such as an arithmetic logic unit, a microprocessor, a general purpose controller, a specialized processing unit, or some other processor array to perform computations and provide electronic display signals to a display device (not shown). The processor 802 can process data signals and may include various computing architectures including a complex instruction set computer (CISC) architecture, a reduced instruction set computer (RISC) architecture, an architecture implementing a combination of instruction sets, etc. In some embodiments, the processor 802 may include one or more general processors, special-purpose processing devices such as an application specific integrated circuit (ASIC), a field programmable gate array (FPGA), a digital signal processor (DSP), network processor, or the like. Although FIG. 8A depicts a single processor 802, multiple processors 802 may be included. Other processors, operating systems, sensors, displays and physical configurations are possible.

The memory 804 can include one or more non-transitory computer-readable media for storing instructions and/or data that can be executed by the processor 802. The instructions and/or data may include code for performing the techniques described herein. In some embodiments, the memory 804 may store the detector 810. The memory 804 may include a dynamic random access memory (DRAM) device, a static random access memory (SRAM) device, embedded memory, flash memory, or some other memory device. In some embodiments, the memory 804 can also include a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

The communication unit 808 can transmit and receive data to and from the server 852 and/or the computing device 801. The communication unit 808 may be coupled (wiredly, wirelessly, etc.) to the network 850 to communicate with other entities forming the network 850. In some embodiments, the communication unit 808 may include one or more ports for direct physical connection to the network 850 or to another communication channel. For example, the communication unit 808 may include a USB, SD, CAT-5 or similar port for wired communication with the server 852 and/or the computing device 801. In some embodiments, the communication unit 808 may include a wireless transceiver for exchanging data with the server 852 or other communication channels using one or more wireless communication methods, including IEEE 802.11, IEEE 802.16, BLUETOOTH®, dedicated short-range communications (DSRC) or another suitable wireless communication method.

In some embodiments, the communication unit 808 can include a cellular communications transceiver for sending and receiving data over a cellular communications network including via short messaging service (SMS), multimedia messaging service (MMS), hypertext transfer protocol (HTTP), direct data connection, WAP, e-mail or another suitable type of electronic communication. In some embodiments, the communication unit 808 can include a wired port and a wireless transceiver. The communication unit 808 can also provide other conventional connections to the network 850 for distribution of files and/or media objects using standard network protocols including TCP/IP, HTTP, HTTPS, and SMTP, etc.

The video capture device 812 is any device capable of capturing one or more moving visual images and converting them into a format such that they appear to be continuous to a user. Non-limiting examples of the video capture device 812 may include a video recorder, a camcorder, a webcam, a camera, etc. The audio capture device 812 is any device capable of capturing one or more audible components including, for example, a user speech, a voice command, a song, or any other sound effect. Non-limiting examples of the audio capture device 814 may include a microphone, a sensor, or the like. The image capture device 816 is any device capable of capturing one or more still images in its surrounding environment. Non-limiting examples of the image capture device 816 may include a webcam, a camera, a sensor, etc. The one or more capturing devices referred to herein may include in various embodiments one or more of the video capture device 812, the audio capture device 812, and the image capture device 816.

The detector 810 may detect a sound source of interest at its accurate location in a shared auditory space and guide a mobile computing device, such as a robot to the sound source of interest using the location. As depicted, the detector 810 may include the detector layer 102, the synchronization layer 104, and the fusion layer 106 as described above with respect to FIG. 1. As depicted, the detector 810 is shown with dashed lines to indicate that the detector 810 is not an integral part of the computing device 801 and that it may be included in other entities connected to the network 850. For instance, an instance of the detector 810 may be included in the server 852, which may include on or more of the components and/or be configured to perform one or more of the acts and/or functionalities of the detector 810.

The server 852 may include one or more computing devices having data processing, storing, and communication capabilities. For example, the server 852 may include one or more hardware servers, server arrays, storage devices and/or systems, etc. In some embodiments, the server 852 may include one or more virtual servers, which operate in a host server environment and access the physical hardware of the host server including, for example, a processor, memory, storage, network interfaces, etc., via an abstraction layer (e.g., a virtual machine manager).

In the depicted illustration, the server 852 include an application 854 operable to provide various computing functionalities, services, and/or resources, and to send data to and receive data from the other entities of the network 850, such as the computing device 801. For example, the application 854 may provide functionality for user account management; internet searching; social networking; web-based email; word-processing; banking; finance; blogging; micro-blogging; photo management; video, music and multimedia hosting, distribution, and sharing; business services; news and media distribution; any combination of the foregoing services; etc. It should be understood that the server 852 is not limited to providing the above-noted services and may include other network-accessible service.

The application 854 may transmit electronic files and/or data embodying the services it provides to the computing device 801 for rendering. In some implementations, the electronic files and/or data streams may be formatted using a markup language(s) or other processing (e.g., HTML, XML, JSON, etc.), style sheet(s) (e.g., CSS, XSL, etc.), graphic(s) (e.g., PNG, JPG, GIF, etc.), and/or scripts (e.g., JavaScript, ActionScript, etc.), and the computing device 801 may interpret and/or execute processes in association with the electronic files and/or data streams and/or render an interactive Web User Interface (WUI) for presentation to a user based on the electronic files and/or data streams.

Figure 8C:
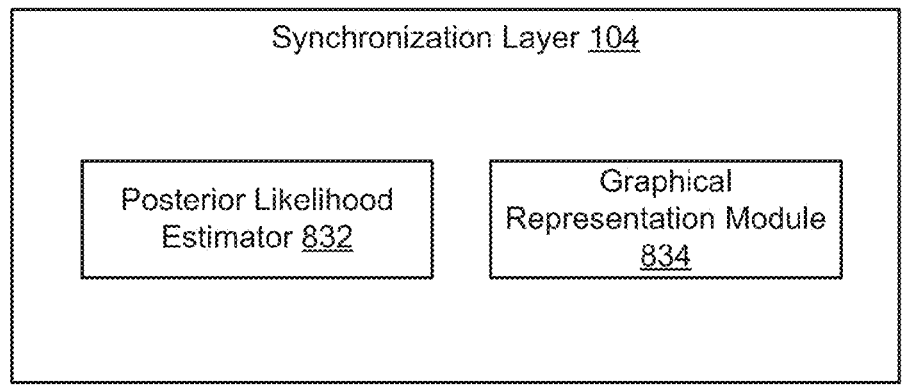
FIG. 8C is a block diagram of an example synchronization layer.
Figure 8D:
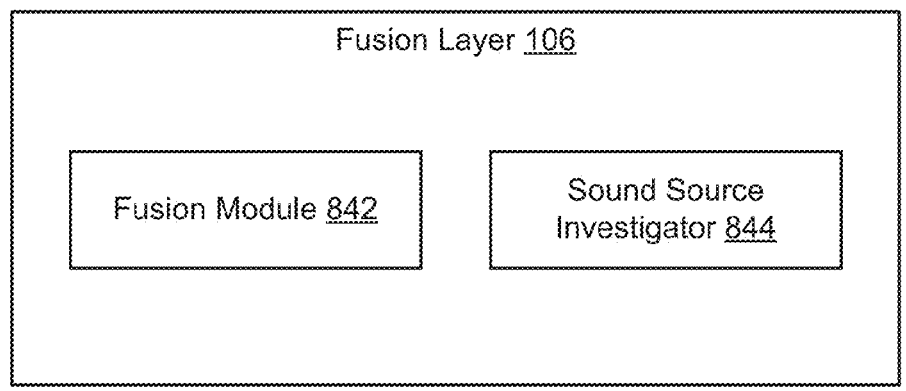
FIG. 8D is a block diagram of an example fusion layer.

FIGS. 8B-8D illustrates various software components that are associated with the detection layer 102, the synchronization layer 104, and the fusion layer 106, respectively. In particular, the detection layer 102 (as depicted in FIG. 8B) includes a sound source localization module 822, a gesture detection module 824, a speech recognition module 826, and a body pose estimation module 828. The synchronization layer 104 (as depicted in FIG. 8C) includes a posterior likelihood estimator 832 and a graphical representation module 834. The fusion layer 106 (as depicted in FIG. 8D) includes a fusion module 842 and a sound source investigator 844. These components 822, 824, 826, 828, 832, 834, 842, and/or 844 are described in detail with respect to at least FIG. 1 and methods 200 and 300, and hence the description for these components will not be repeated here.

The components 822, 824, 826, 828, 832, 834, 842, and/or 844 may be communicatively coupled by the bus 806 and/or the processor 802 to one another and/or the other components 804, 808, 812, 814, and/or 816 of the computing device 801. In some embodiments, one or more of the components 822, 824, 826, 828, 832, 834, 842, and/or 844 are sets of instructions executable by the processor 802 to provide their functionality. In other embodiments, one or more of the components 822, 824, 826, 828, 832, 834, 842, and/or 844 are stored in the memory 804 of the computing device 801 and are accessible and executable by the processor 802 to provide their functionality. In any of the foregoing embodiments, these components 822, 824, 826, 828, 832, 834, 842, and/or 844 may be adapted for cooperation and communication with the processor 802, other components of the computing device 801, and/or the server 852. In various embodiments, these components may be implemented via software, hardware, firmware, a combination of the foregoing, etc.

Example Scenarios

Figure 13:
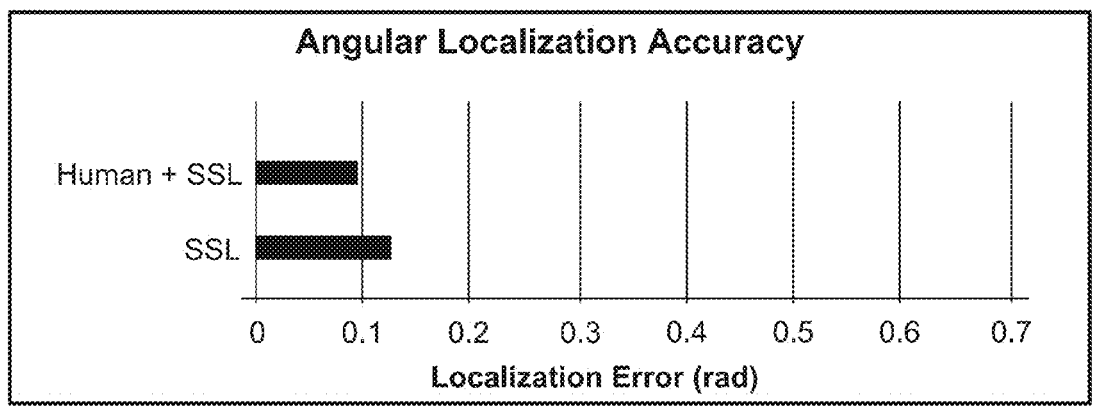
FIG. 13 is an example graph illustrating average angular localization error associated with various sound source detection components in an example scenario.

Scenario 1 illustrates the effectiveness of combining speech, pointing, and computational SSL components for sound source detection. In this scenario, a single loud source (60 dB) was used in a shared auditory environment. FIG. 13 summarizes angular localization error associated position determined based on SSL alone, and position determined based on combining speech and pointing likelihoods first, scaling the combined likelihoods, and adding the scaled combined likelihoods (referring in figure to as Human) to the SSL component. Advantageously, as depicted, using the SSL alone had an average error of approximately 0.13 (rad) while using the combined likelihoods plus the SSL likelihood had an error of only 0.09 (rad), an improvement of 0.04 (rad) over SSL alone.

Figure 14A:
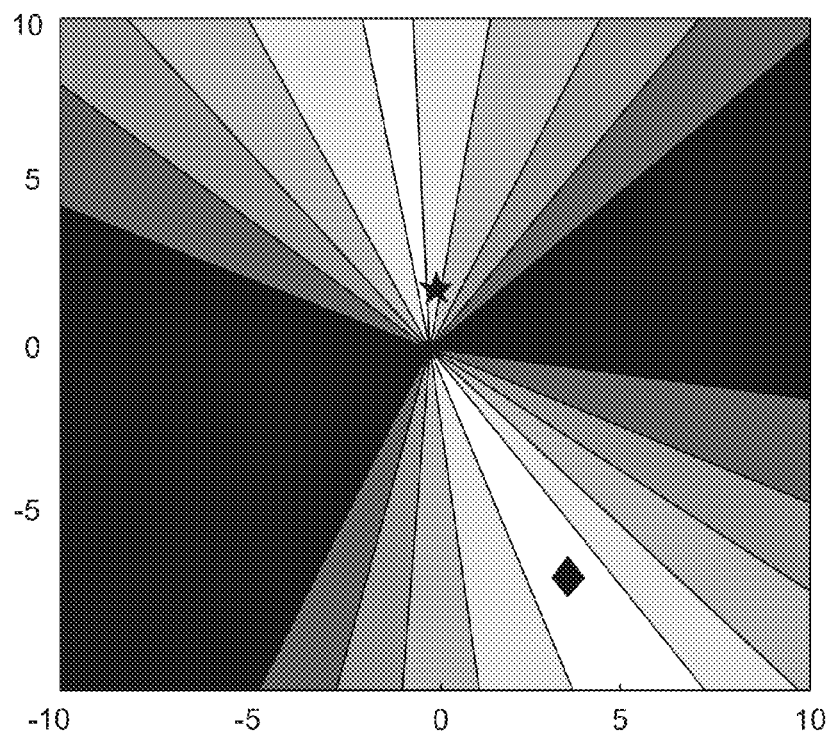
FIG. 14A depicts a sound source location estimation using only computation sound source localization given multiple sound sources present in an environment.
Figure 14B:
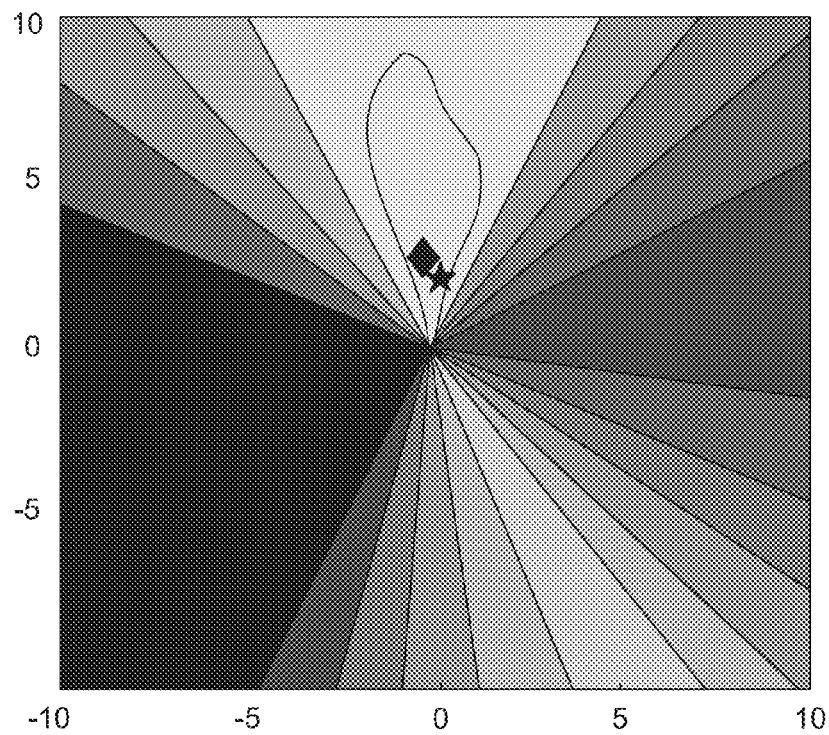
FIG. 14B depicts a sound source location estimation using a combination of computation sound source localization and one or more user inputs given multiple sound sources present in an environment.

Scenario 2 further illustrates the effectiveness of combining speech, pointing, and computational SSL components for sound source detection in comparison to detecting the sound source using each of these components individually. In this scenario, multiple sound sources were used in a shared auditory environment. FIG. 14A depicts sound source location estimated using computational SSL alone. In this figure, a star represents a correct sound source location and a diamond represents a location estimated using SSL. As shown, the computational SSL alone is not effective for determining the position of the sound source in a multiple sound source environment. In contrast, FIG. 14B depicts that combining pointing and speech with the computational SSL as described herein is an effective approach for determining the position of the sound source in a multiple sound source environment.

In the above description, for purposes of explanation, numerous specific details are set forth in order to provide a thorough understanding of the specification. It should be understood, however, that the disclosure can be practiced without these specific details. In some embodiments, structures and devices are shown in block diagram form in order to avoid obscuring the description. For example, various embodiments are described primarily with reference to user interfaces and particular hardware. However, the embodiments apply to any type of computing device that can receive data and commands, and any peripheral devices providing services.

Reference in the specification to "an embodiment" or "some embodiments" means that a particular feature, structure, or characteristic described in connection with the embodiment(s) is included in at least one embodiment of the description. The appearances of the phrase "in one embodiment" in various places in the specification are not necessarily all referring to the same embodiment.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The specification also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The specification can take the form of an entirely hardware embodiment, an entirely software embodiment or an embodiment containing both hardware and software elements. In a preferred embodiment, the specification is implemented in software, which includes but is not limited to firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats. Furthermore, as will be apparent to one of ordinary skill in the relevant art, the modules, routines, features, attributes, methodologies and other aspects of the disclosure can be implemented as software, hardware, firmware or any combination of the three. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the disclosure is in no way limited to implementation in any specific programming language, or for any specific operating system or environment. Accordingly, the disclosure is intended to be illustrative, but not limiting, of the scope of the subject matter set forth in the following claims.

What is claimed is:

1. A computer-implemented method comprising:
   receiving, using one or more computing devices, one or more user inputs;
   capturing, using the one or more computing devices, a sound associated with a sound source via one or more capturing devices using sound source localization;
   estimating, using the one or more computing devices, one or more first posterior likelihoods of one or more positions of the sound source based on the one or more user inputs;
   estimating, using the one or more computing devices, a second posterior likelihood of a position of the sound source based on the sound; and
   estimating, using the one or more computing devices, an overall posterior likelihood of an actual position of the sound source based on 1) the one or more first posterior likelihoods of the one or more positions of the sound source estimated based on the one or more user inputs and 2) the second posterior likelihood of the position of the sound source estimated based on the sound.

2. The computer-implemented method of claim 1, wherein estimating the overall posterior likelihood further includes:
   fusing, using the one or more computing devices, the one or more first posterior likelihoods of the one or more positions of the sound source and the second posterior likelihood of the position of the sound source to produce the overall posterior likelihood.

3. The computer-implemented method of claim 2, wherein the one or more first posterior likelihoods include two or more posterior likelihoods estimated based on two or more user inputs, and fusing the two or more first posterior likelihoods and the second posterior likelihood includes:
   combining, using the one or more computing devices, the two or more first posterior likelihoods into a combined posterior likelihood;
   scaling, using the one or more computing devices, the combined posterior likelihood; and
   combining the scaled combined posterior likelihood with the second posterior likelihood.

4. The computer-implemented method of claim 1, wherein the one or more user inputs include one or more of a user gesture, a user speech segment, and a user body pose.

5. The computer-implemented method of claim 1, wherein
the one or more user inputs include a user gesture and a user body pose,
receiving the one or more user inputs further includes determining a gesturing direction from the user gesture and determining one or more of a position and orientation from the user body pose, and
estimating the one or more first posterior likelihoods further includes estimating a gesture-pose-based posterior likelihood of a position of the sound source based on the gesturing direction and the one or more of the position and orientation associated with the user body pose.

6. The computer-implemented method of claim 1, wherein
the one or more inputs include a user speech segment and a user body pose;
receiving the one or more user inputs further includes determining a direction from the user speech segment and determining one or more of a position and orientation from the user body pose, and
estimating the one or more first posterior likelihoods further includes estimating a speech-pose-based posterior likelihood of a position of the sound source based on the direction associated with the speech segment and the one or more of the position and orientation associated with the user body pose.

7. The computer-implemented method of claim 1, wherein
estimating the one or more first posterior likelihoods further includes generating one or more first evidence grids of likely sound source positions based on the one or more user inputs, the one or more first evidence grids reflecting the one or more first posterior likelihoods, respectively,
estimating the second posterior likelihood further includes generating a second evidence grid of likely sound source positions based on the sound, the second evidence grid reflecting the second posterior likelihood, and
estimating the overall posterior likelihood of the actual position of the sound source further includes combining the one or more first evidence grids and the second evidence grid.

8. The computer-implemented method of claim 1, further comprising:
guiding, using the one or more computing devices, a mobile computing device to the actual position of the sound source.

9. The computer-implemented method of claim 1, wherein the one or more capturing devices includes one or more of an image capturing device, a video capturing device, and an audio capturing device.

10. A computer program product comprising a non-transitory computer-readable medium storing a computer-readable program, wherein the computer-readable program, when executed on one or more computing devices, causes the one or more computing devices to:
receive one or more user inputs;
capture a sound associated with a sound source via one or more capturing devices using sound source localization;
estimate one or more first posterior likelihoods of one or more positions of the sound source based on the one or more user inputs;
estimate a second posterior likelihood of a position of the sound source based on the sound; and
estimate an overall posterior likelihood of an actual position of the sound source based on 1) the one or more first posterior likelihoods of the one or more positions of the sound source estimated based on the one or more user inputs and 2) the second posterior likelihood of the position of the sound source estimated based on the sound.

11. The computer program product of claim 10, wherein to estimate the overall posterior likelihood further includes:
fusing the one or more first posterior likelihoods of the one or more positions of the sound source and the second posterior likelihood of the position of the sound source to produce the overall posterior likelihood.

12. The computer program product of claim 11, wherein the one or more first posterior likelihoods include two or more posterior likelihoods estimated based on two or more user inputs, and to fuse the two or more first posterior likelihoods and the second posterior likelihood includes:
combining the two or more first posterior likelihoods into a combined posterior likelihood;
scaling the combined posterior likelihood; and
combining the scaled combined posterior likelihood with the second posterior likelihood.

13. The computer program product of claim 10, wherein the one or more user inputs include one or more of a user gesture, a user speech segment, and a user body pose.

14. The computer program product of claim 10, wherein
the one or more user inputs include a user gesture and a user body pose,
to receive the one or more user inputs further includes determining a gesturing direction from the user gesture and determining one or more of a position and orientation from the user body pose, and
to estimate the one or more first posterior likelihoods further includes estimating a gesture-pose-based posterior likelihood of a position of the sound source based on the gesturing direction and the one or more of the position and orientation associated with the user body pose.

15. The computer program product of claim 10, wherein
the one or more inputs include a user speech segment and a user body pose;
to receive the one or more user inputs further includes determining a direction from the user speech segment and determining one or more of a position and orientation from the user body pose, and
to estimate the one or more first posterior likelihoods further includes estimating a speech-pose-based posterior likelihood of a position of the sound source based on the direction associated with the speech segment and the one or more of the position and orientation associated with the user body pose.

16. The computer program product of claim 10, wherein
to estimate the one or more first posterior likelihoods further includes generating one or more first evidence grids of likely sound source positions based on the one or more user inputs, the one or more first evidence grids reflecting the one or more first posterior likelihoods, respectively,
to estimate the second posterior likelihood further includes generating a second evidence grid of likely sound source positions based on the sound, the second evidence grid reflecting the second posterior likelihood, and
to estimate the overall posterior likelihood of the actual position of the sound source further includes combining the one or more first evidence grids and second evidence grid.

17. The computer program product of claim 10, wherein the computer-readable program, when executed on the one or more computing devices, causes the one or more computing devices to:
guide a mobile computing device to the actual position of the sound source.

18. The computer program product of claim 10, wherein the one or more capturing devices includes one or more of an image capturing device, a video capturing device, and an audio capturing device.

19. A system comprising:
one or more processors; and
one or more memories storing instructions that, when executed by the one or more processors, cause the system to:
receive one or more user inputs;
capture a sound associated with a sound source via one or more capturing devices using sound source localization;
estimate one or more first posterior likelihoods of one or more positions of the sound source based on the one or more user inputs;
estimate a second posterior likelihood of a position of the sound source based on the sound; and
estimate an overall posterior likelihood of an actual position of the sound source based on 1) the one or more first posterior likelihoods of the one or more positions of the sound source estimated based on the one or more user inputs and 2) the second posterior likelihood of the position of the sound source estimated based on the sound.

20. The system of claim 19, wherein to estimate the overall posterior likelihood further includes:
fusing the one or more first posterior likelihoods of the one or more positions of the sound source and the second posterior likelihood of the position of the sound source to produce the overall posterior likelihood.

21. The system of claim 20, wherein the one or more first posterior likelihoods include two or more posterior likelihoods estimated based on two or more user inputs, and to fuse the two or more first posterior likelihoods and the second posterior likelihood includes:
combining the two or more first posterior likelihoods into a combined posterior likelihood;
scaling the combined posterior likelihood; and
combining the scaled combined posterior likelihood with the second posterior likelihood.

22. The system of claim 19, wherein the one or more user inputs include one or more of a user gesture, a user speech segment, and a user body pose.

23. The system of claim 19, wherein
the one or more user inputs include a user gesture and a user body pose,
to receive the one or more user inputs further includes determining a gesturing direction from the user gesture and determining one or more of a position and orientation from the user body pose, and
to estimate the one or more first posterior likelihoods further includes estimating a gesture-pose-based posterior likelihood of a position of the sound source based on the gesturing direction and the one or more of the position and orientation associated with the user body pose.

24. The system of claim 19, wherein
the one or more inputs include a user speech segment and a user body pose;
to receive the one or more user inputs further includes determining a direction from the user speech segment and determining one or more of a position and orientation from the user body pose, and
to estimate the one or more first posterior likelihoods further includes estimating a speech-pose-based posterior likelihood of a position of the sound source based on the direction associated with the speech segment and the one or more of the position and orientation associated with the user body pose.

25. The system of claim 19, wherein
to estimate the one or more first posterior likelihoods further includes generating one or more first evidence grids of likely sound source positions based on the one or more user inputs, the one or more first evidence grids reflecting the one or more first posterior likelihoods, respectively,
to estimate the second posterior likelihood further includes generating a second evidence grid of likely sound source positions based on the sound, the second evidence grid reflecting the second posterior likelihood, and
to estimate the overall posterior likelihood of the actual position of the sound source further includes combining the one or more first evidence grids and the second evidence grid.

26. The system of claim 19, wherein the computer-readable program, when executed on the one or more computing devices, causes the one or more computing devices to:
guide a mobile computing device to the actual position of the sound source.

27. The system of claim 19, wherein the one or more capturing devices includes one or more of an image capturing device, a video capturing device, and an audio capturing device.

* * * * *